United States Patent
Tsui et al.

(10) Patent No.: US 12,350,484 B2
(45) Date of Patent: Jul. 8, 2025

(54) IMPLANTABLE CO-PULSATILE EPI-VENTRICULAR CIRCULATORY SUPPORT SYSTEM WITH SUTURELESS FLOW CANNULA ASSEMBLY

(71) Applicant: 3R Life Sciences Corporation, Campbell, CA (US)

(72) Inventors: Steven Shi Lap Tsui, Kaohsiung (TW); Pong-Jeu Lu, Kaohsiung (TW)

(73) Assignee: 3R LIFE SCIENCES CORPORATION, Campbell, CA (US)

( * ) Notice: Subject to any disclaimer, the term of this patent is extended or adjusted under 35 U.S.C. 154(b) by 488 days.

(21) Appl. No.: 17/695,376

(22) Filed: Mar. 15, 2022

(65) Prior Publication Data

US 2022/0296878 A1 Sep. 22, 2022

Related U.S. Application Data

(60) Provisional application No. 63/162,086, filed on Mar. 17, 2021, provisional application No. 63/162,098, filed on Mar. 17, 2021.

(51) Int. Cl.
*A61M 60/863* (2021.01)
*A61M 60/165* (2021.01)
(Continued)

(52) U.S. Cl.
CPC ........ *A61M 60/863* (2021.01); *A61M 60/165* (2021.01); *A61M 60/178* (2021.01); *A61M 60/268* (2021.01); *A61M 60/31* (2021.01); *A61M 60/32* (2021.01); *A61M 60/427* (2021.01); *A61M 60/515* (2021.01);
(Continued)

(58) Field of Classification Search
CPC .............. A61M 60/531; A61M 60/427; A61M 60/859; A61M 60/857; A61M 60/861; A61M 60/515; A61M 60/165; A61M 60/268

See application file for complete search history.

(56) References Cited

U.S. PATENT DOCUMENTS

2006/0167333 A1   7/2006 Moore et al.
2006/0229488 A1*  10/2006 Ayre ................... A61M 60/857
                                                        600/17

(Continued)

OTHER PUBLICATIONS

International Searching Authority and Written Opinion issued Jun. 16, 2022 in PCT Application No. PCT/US22/020409.

*Primary Examiner* — Rex R Holmes
*Assistant Examiner* — Jennifer L Ghand
(74) *Attorney, Agent, or Firm* — MUNCY, GEISSLER, OLDS & LOWE, P.C.

(57) ABSTRACT

An implantable circulatory support system, configured to connect a ventricular chamber of a heart, including a valveless displacement blood pump, a deformable polymeric flow cannula, a pair of male and female fasteners, a coupler, a driveline assembly, and a co-pulsatile driver. Forward and backward flow communication between the blood pump and the heart chamber is accomplished using the present flow cannula invention which is anastomosed to the heart chamber in a sutureless manner. When providing circulatory support, the co-pulsatile driver ejects blood out of the blood pump during systolic ventricular contraction and fills the blood pump with blood during diastolic ventricular relaxation.

6 Claims, 29 Drawing Sheets

(51) Int. Cl.
    *A61M 60/178*     (2021.01)
    *A61M 60/268*     (2021.01)
    *A61M 60/31*     (2021.01)
    *A61M 60/32*     (2021.01)
    *A61M 60/427*     (2021.01)
    *A61M 60/515*     (2021.01)
    *A61M 60/531*     (2021.01)
    *A61M 60/546*     (2021.01)
    *A61M 60/585*     (2021.01)
    *A61M 60/857*     (2021.01)
    *A61M 60/859*     (2021.01)
    *A61M 60/861*     (2021.01)
    *A61M 60/878*     (2021.01)

(52) U.S. Cl.
    CPC ........ *A61M 60/531* (2021.01); *A61M 60/546* (2021.01); *A61M 60/585* (2021.01); *A61M 60/857* (2021.01); *A61M 60/859* (2021.01); *A61M 60/861* (2021.01); *A61M 60/878* (2021.01); *A61M 2205/02* (2013.01)

(56) References Cited

U.S. PATENT DOCUMENTS

| | | |
|---|---|---|
| 2006/0235357 A1 | 10/2006 | Woodward et al. |
| 2007/0055358 A1 | 3/2007 | Krolik et al. |
| 2008/0300447 A1 | 12/2008 | Lu et al. |
| 2011/0118766 A1 | 5/2011 | Reichenbach et al. |
| 2015/0104331 A1 | 4/2015 | Dye |
| 2018/0050143 A1 | 2/2018 | Nguyen et al. |

\* cited by examiner

IMPLANTABLE CO-PULSATILE EPI-VENTRICULAR CIRCULATORY SUPPORT SYSTEM WITH SUTURELESS FLOW CANNULA ASSEMBLY

BACKGROUND OF THE INVENTION

Field of the Invention

The application relates in general to an implantable circulatory support system, and in particular to a co-pulsatile support system that includes a sutureless flow cannula assembly.

Description of the Related Art

Mechanical circulatory support system such as ventricular assist device (VAD), in particular left ventricular assist device (LVAD), has evolved into a standard care modality for treating advanced heart failure (HF). Currently, the patients indicated for VAD therapy are those who are unresponsive to medical therapy, being classified as terminal stage heart failure with imminent death threat if without heart transplant or mechanical circulatory support. To date, the worldwide VAD registry has exceeded 25,000 implants since the approval of the continuous-flow durable LVADs (rotary blood pumps) including HeartMate 2, HeartMate 3 and HeartWare HVAD. It is anticipated that the use of LVADs as advanced heart failure therapy will be increasingly accepted along with further technologies advancement.

Conventionally heart failure can be categorized into systolic pump failure and diastolic pump failure. Ejection fraction (EF), defined as the blood volume ejected out from the ventricle divided by the maximum blood volume stored in the ventricular chamber, has been used to quantify the contractility of the heart. For a normal human, EF is around 70% at rest. As for systolic heart failure, EF is generally lower than 40%, manifested with a pathologically dilated ventricular chamber and reduced wall thickness. Such enlarged chamber, according to Laplace law, consumes more contractile energy in the myocardium to deliver stroke output, hence making ventricular contraction inadequate and inefficient. Diastolic heart failure, however, is caused by chamber filling dysfunction, of which the myocardial wall is unusually stiff and thick, causing impaired blood filling capacity leading to cardiac output shortage, albeit the EF is about normal. Systolic heart failure, or heart failure with reduced ejection fraction (HFrEF), is understood relatively clearer and the therapies, either by medical or by device treatment, are reasonably well established. On the other hand, heart failure with preserved ejection fraction (HFpEF), a broader disease condition encompassing diastolic heart failure and other non-cardiac comorbidities, has gained attention in recent years. However, its pathophysiology is less well understood and available treatments are less effective. Patients with HFpEF account for approximately half of the mortality count of all-cause heart failure death toll. The epidemiologic burden of mortality and hospitalization caused by HFpEF is rising, and the growing elderly population is predicted to worsen this healthcare burden trend.

As classified by EF, heart failure patients with EF<40% are taken as HFrEF, and patients having borderline or even normal EF, namely EF>40-50%, are classified as belonging to the HFpEF cohort. Effort has been exerted over two decades in search of HFpEF phenotyping and the corresponding therapy. More than twenty or so medical trials have been conducted, but none of the medicines available was proven to be effective in treating HFpEF. The causal factor of HFpEF is heterogenous, patients died of both cardiac and non-cardiac reasons. It has been shown that causal factors leading to HFpEF mortality include pulmonary hypertension, edema, right ventricle (RV) failure, atrial fibrillation, systemic hypertension, ventricular-vascular stiffening, and non-cardiac factors like obesity, anemia, diabetes mellitus and renal dysfunction.

Both HFrEF and HFpEF share the same characteristic of disease progression, namely, a vicious circle with deterioration toward death. Device intervention, currently, probably is the more effective treatment option other than medical therapy that seemingly is only administered for management of diuretics and treatment of comorbidities. Rotary blood pumps that gained popularity in recent years are only indicated for systolic heart failure with EF<40%, and the inclusion criteria require patients to have sufficient right heart reserve. Statistically, around 30-40% rotary pump recipients will develop device-induced right heart failure after LVAD implantation. It is unlikely that the current continuous-flow LVAD would be beneficial to HFpEF patients who usually have restricted dimensions of the left ventricular cavity. For a LVAD to effectively treat HFpEF, it has to be developed with a different design concept that addresses the disease characteristics associated with HFpEF. To date, there exists no device therapy for treating HFpEF. It can be said that the understanding of pathophysiology of HFpEF and identification of treatment methods addressing the causal factors, both pharmaceutically and mechanistically, are urgently needed.

BRIEF SUMMARY OF INVENTION

To address the limitations of conventional circulatory support products, an embodiment of the invention configured to connect a heart chamber and a blood pump, including a flow cannula and a pair of male and female fasteners are provided. The flow cannula includes a conduit body, a bellmouth and a flange ramp portion, wherein the conduit body is between the bellmouth and the flange ramp portion. The bellmouth is at the first end of the flow cannula and is configured to be inserted into the heart chamber; the flange ramp portion is at the second end of the flow cannula and is configured to be interfaced to the blood bump assembly. The inner surface of the flow cannula is smooth and seamless. The pair of male fastener and female fastener is screw interconnected, wherein the male fastener is anchored on the flow cannula, and the female fastener is compressed against the epicardium of the heart.

In some embodiments, the flow cannula has a stent, embedded within the wall of the flow cannula.

In some embodiments, the stent is inside the conduit body and the bellmouth.

In some embodiments, the stent has an array of zig-zag rings, a connecting portion, and cone-shaped stent rings, wherein connecting portion connects the array of zig-zag rings which is inside the conduit body and the cone-shaped stent rings which are inside the bellmouth.

In some embodiments, the bellmouth has a gradually thinning wall thickness toward the tip of the bellmouth, and the tip is literally sharp-edged.

In some embodiments, the outer surface of the flow cannula configured for contact with the myocardium of the heart is roughened or is covered with a porous material to promote cell and tissue ingrowth.

In some embodiments, the female fastener has a female fastener cap configured for contact with the epicardium for promoting cell and tissue ingrowth for hemostasis and immobilization purposes, wherein porous materials are attached to the female fastener cap.

In some embodiments, the female fastener has a cushion cuff, wherein the cushion cuff is around and attached an outer rim of the female fastener cap, and is in contact with the epicardium.

In some embodiments, the conduit body has multiple protruded seats protruded from an outside wall of the conduit body; wherein the male fastener has multiple through slots respectively corresponding to the protruded seats; wherein the protruded seats are engaged with the through slots.

In some embodiments, the flow cannula has deformable polymeric material.

In some embodiments, the conduit body of the flow cannula is curved or bendable.

Another embodiment of the invention provides an implantable circulatory support system, including a valveless displacement blood pump, a deformable polymeric flow cannula, a pair of male and female fasteners, a coupler, a driveline assembly, and a co-pulsatile driver. The blood pump includes a blood sac, a blood pump housing, a stem suspension integrating the blood sac within the blood pump housing, a sensor embedded in the blood pump housing to track the cardiac cycle, and an inlet adapter with a beak flange. The flow cannula includes a conduit body, a bellmouth and a flange ramp, wherein the conduit body is between the bellmouth and the flange ramp. The bellmouth is at the first end of the flow cannula and is configured to be inserted into a heart chamber, and the flange ramp portion is at the second end of the flow cannula and is configured to be interfaced to the inlet adapter, and an inner surface of the flow cannula is smooth and seamless. The pair of male and female fasteners is screw interconnected, wherein the male fastener is anchored on the flow cannula, and the female fastener is compressed against the epicardium of the heart. The coupler connects the second end of the cannula with the inlet adapter, wherein the coupler includes a flange base and a pair of collars pinned on the flange base, wherein the collars have an internal grooved slot to receive and compress together the flange base, the flange ramp of the flow cannula, and the beak flange of the inlet adapter. The driveline assembly pneumatically communicates the blood pump with as well as transmits the sensor signal to the driver. The co-pulsatile driver commands filling and pneumatic pumping support according to a sensed cardiac cycle, wherein a co-pulsatile pumping is fulfilled by pump ejection during systolic ventricular contraction and pump fill during diastolic ventricular relaxation.

In some embodiments, the flow cannula has a stent, embedded inside the wall of the flow cannula.

In some embodiment, the bellmouth has a gradually thinning wall thickness tapered toward a tip of bellmouth, and the tip is literally sharp-edged.

In some embodiments, the outer surface of the flow cannula configured for contact with the myocardium of the heart is roughened or is covered with a porous material to promote cell and tissue ingrowth.

In some embodiments, the conduit body of the flow cannula is curved or bendable.

In some embodiments, the female fastener has a female fastener cap configured for contact with the epicardium for promoting cell and tissue ingrowth for hemostasis and immobilization purposes, wherein porous materials are attached to the female fastener cap.

In some embodiments, the beak flange of the inlet adapter has a beak interfacing with the flange ramp, and an inner diameter of the beak slightly larger than the inner diameter of the conduit body, and the flange ramp is inclined 30 to 60 degrees to a centerline of the flow cannula.

In some embodiments, the coupler includes an anti-decoupling latch and a collar contour that catches simultaneously onto the entire peripheral rim of the flange base of the coupler during the collars closing for achieving a connection having minimal discontinuities in blood-contacting surfaces.

In some embodiments, the co-pulsatile pumping is fulfilled by referencing to the electrocardiogram.

In some embodiments, the co-pulsatile pumping is fulfilled by referencing to a pressure waveform acquired by the sensor, wherein the sensor is a pressure sensor.

In some embodiments, the stem suspension has a pair of axi-symmetric stems, and the blood sac of the blood pump is made axi-symmetric and supported by the pair of axi-symmetric stems to prolong the durability of the blood pump.

BRIEF DESCRIPTION OF DRAWINGS

The invention can be more fully understood by reading the subsequent detailed description and examples with references made to the accompanying drawings, wherein.

DETAILED DESCRIPTION OF INVENTION

The making and using of the embodiments of the assist devices are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Unless defined otherwise, all technical and scientific terms used herein have the same meaning as commonly understood to one of ordinary skill in the art to which this invention belongs. It should be appreciated that each term, which is defined in a commonly used dictionary, should be interpreted as having a meaning conforming to the relative skills and the background or the context of the present disclosure, and should not be interpreted in an idealized or overly formal manner unless defined otherwise.

Figure 1:
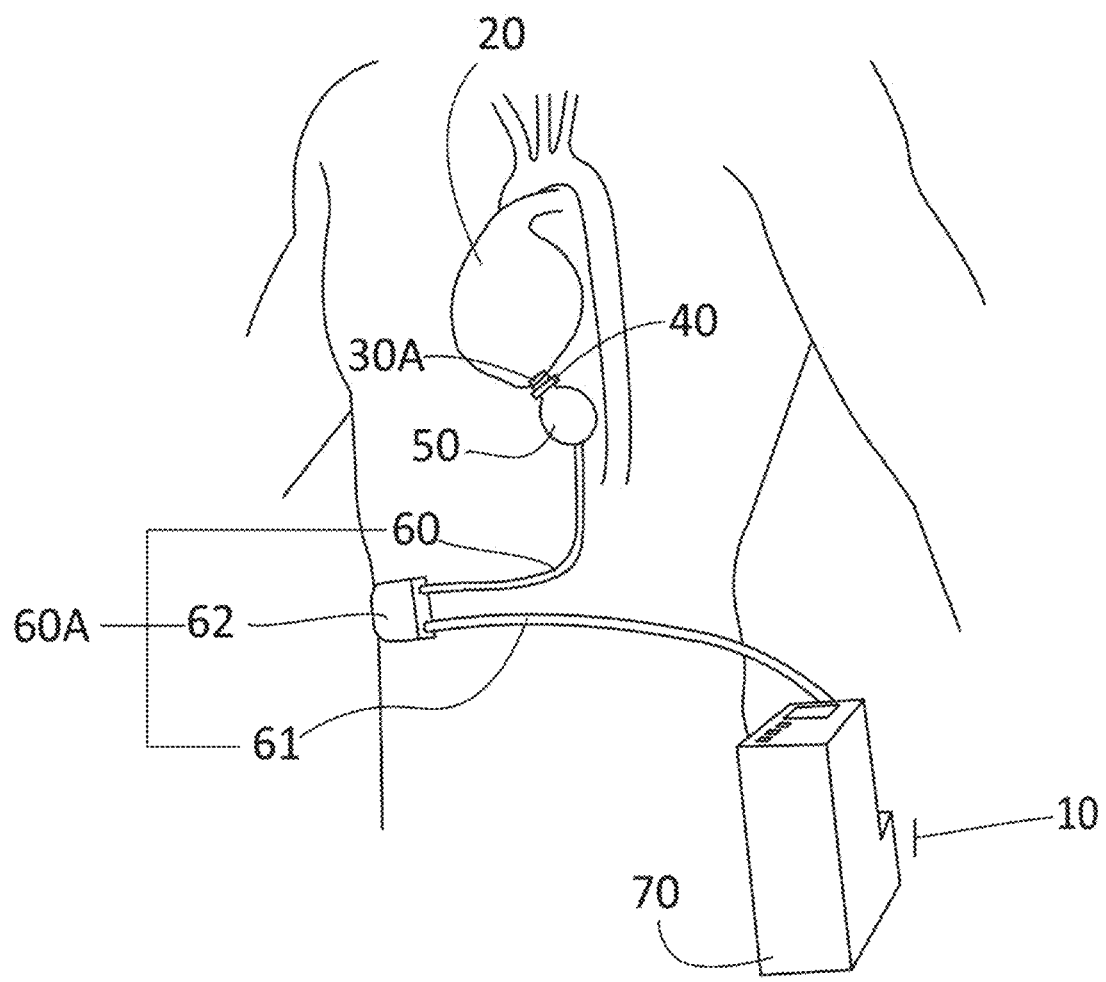
FIG. 1 is a system representation of an implantable epi-ventricular assist device invention comprising a flow cannula, an epi-ventricular blood pump (EVBP), a percutaneous driveline and an external wearable driver.

An embodiment of the present disclosure is directed to an implantable circulatory support system addressing diastolic heart failure, or in a broader sense, the HFpEF. A representative embodiment of invention is shown in FIG. 1, which comprises a flow cannula assembly 30A, a coupler 40, an epi-ventricular blood pump (EVBP or blood pump) 50, a driveline assembly 60A, and an external driver 70. The EVBP 50 is connected via the coupler 40 to a flow cannula 30 of the flow cannula assembly 30A which is implanted in a left ventricle 20. To address the hallmark structural remodeling associated with HFpEF, namely the thickened and stiffened LV myocardial wall with reduced LV chamber volume, an embodiment of the present invention innovates a mechanical volume compensator by adding the actively-regulated blood pump 50, the EVBP, appended to the LV. The anastomotic connection of such EVBP 50 is via a novel flow connector invention (including the flow cannula assembly 30A, the coupler 40) and the operation of the present circulatory support is conducted by a co-pulsatile driving of the EVBP 50, as described below.

Figure 2:
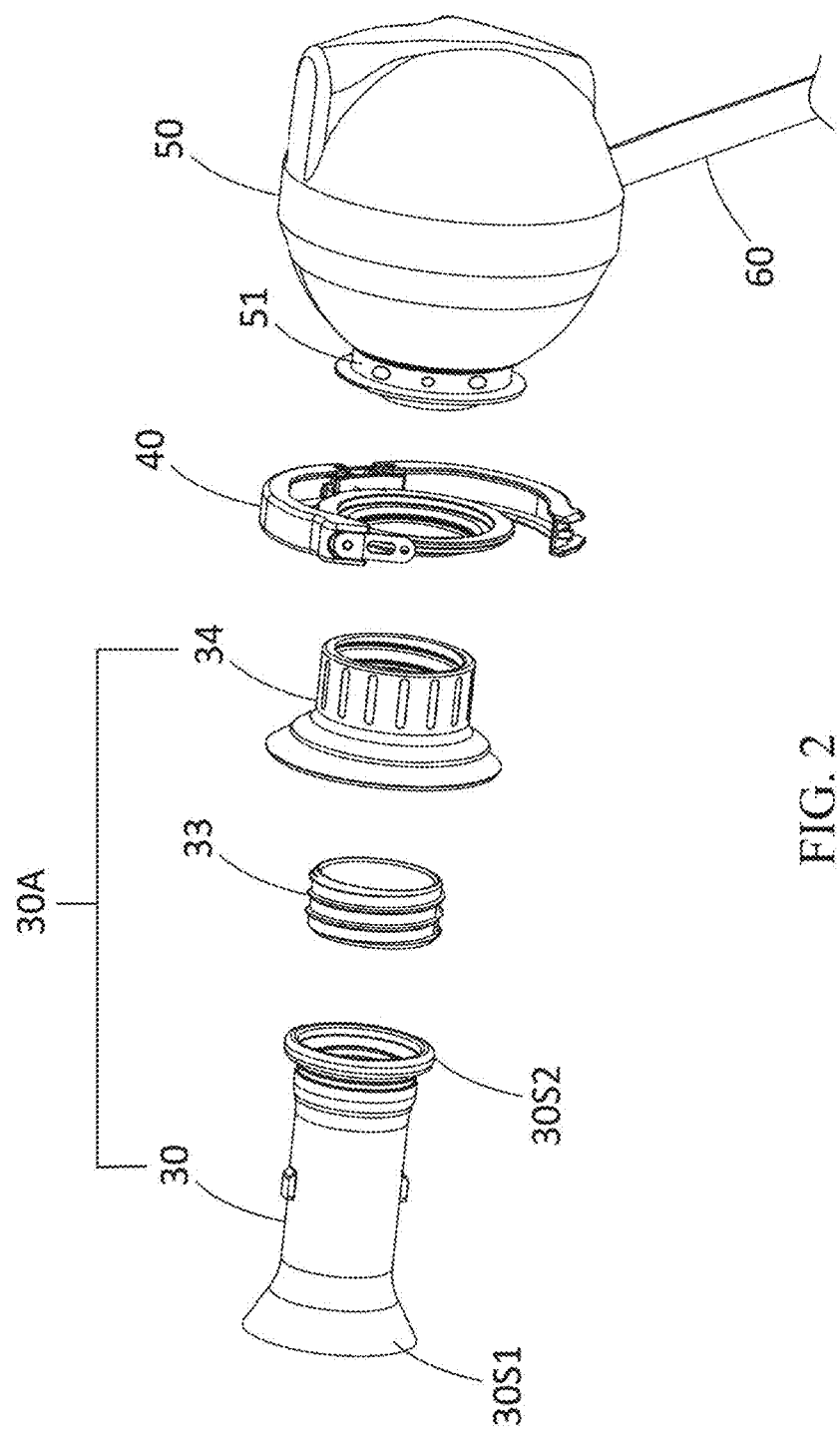
FIG. 2 is an exploded view of implantable subsystems of the epi-ventricular assist device shown in FIG. 1.

An exploded view of the present epi-ventricular assist device implant modules is further illustrated in FIG. 2. The flow cannula assembly 30A has a flow cannula (or a cannula) 30 and the fastener pair 33, 34. The distal end (first end) 30S1 of the flow cannula 30 is funnel-shaped, and the fastener pair 33, 34 is mounted around the flow cannula 30 to achieve a leakage-free fixation of the flow cannula 30 with the heart 20, to be described later. At the proximal end (second end) 30S2 of the flow cannula 30, an integration mechanism incorporating a minimal interface discontinuity design is adopted for connecting the flow cannula 30 with an inlet adapter 51 (see FIG. 10A) of the EVBP 50. In some embodiments, the flow cannula 30 is a deformable polymeric flow cannula.

Figure 3:
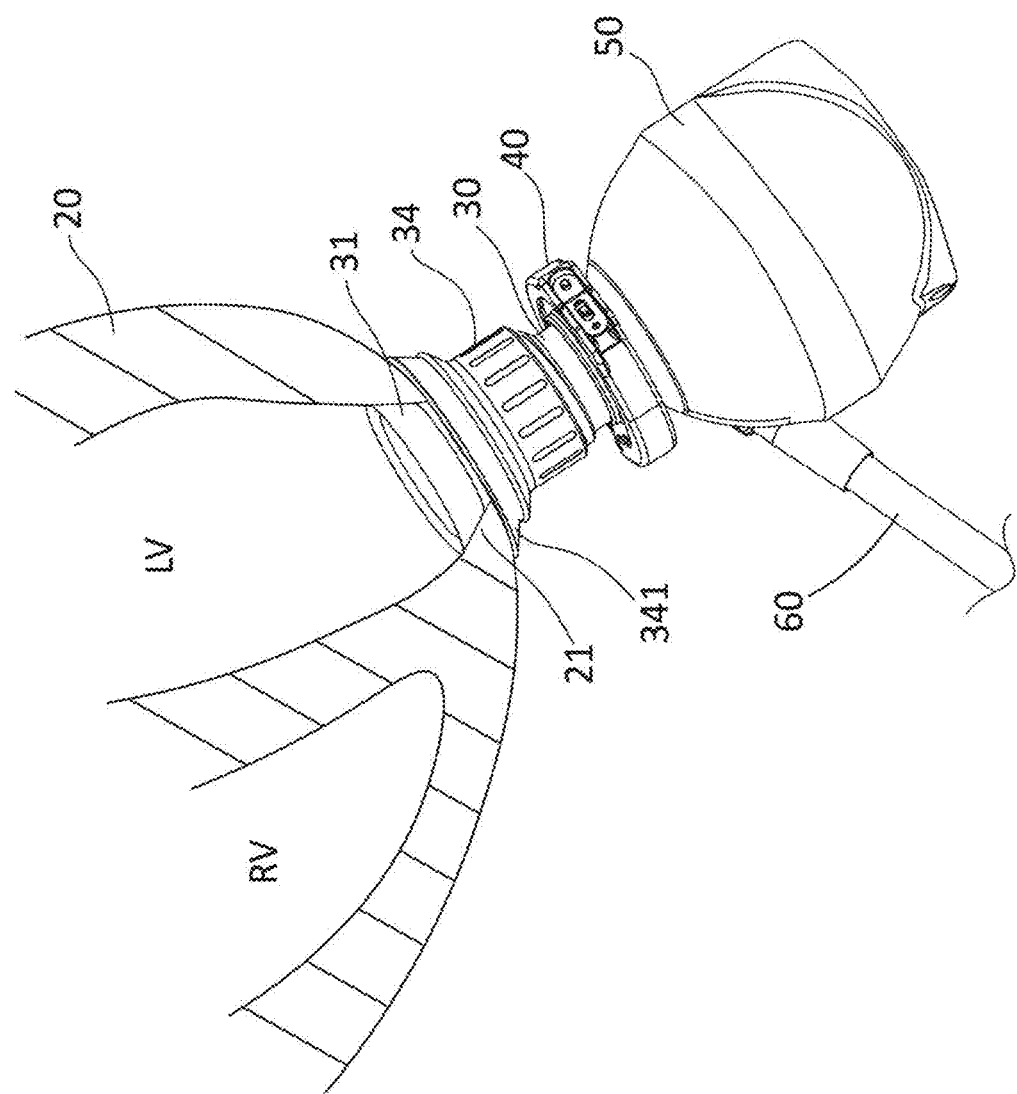
FIG. 3 is an illustration of an epi-ventricular assist device of FIG. 1 with the flow cannula implanted into a left ventricle (wherein LV: left ventricle, RV: right ventricle).

The implantation of the epi-ventricular assist device 100 is shown in FIG. 3. The connection of EVBP 50 to the left ventricle is accomplished by a sutureless connection method. The flow cannula 30 has a bellmouth (or a funnel-shaped conduit) 31 flush-mounted with the endocardium and locked by the female fastener cap 34 exerting compression force to the epicardium, using the bellmouth 31 as a back-stop, for a leakage-free device connection with the heart 20.

Figure 4A:
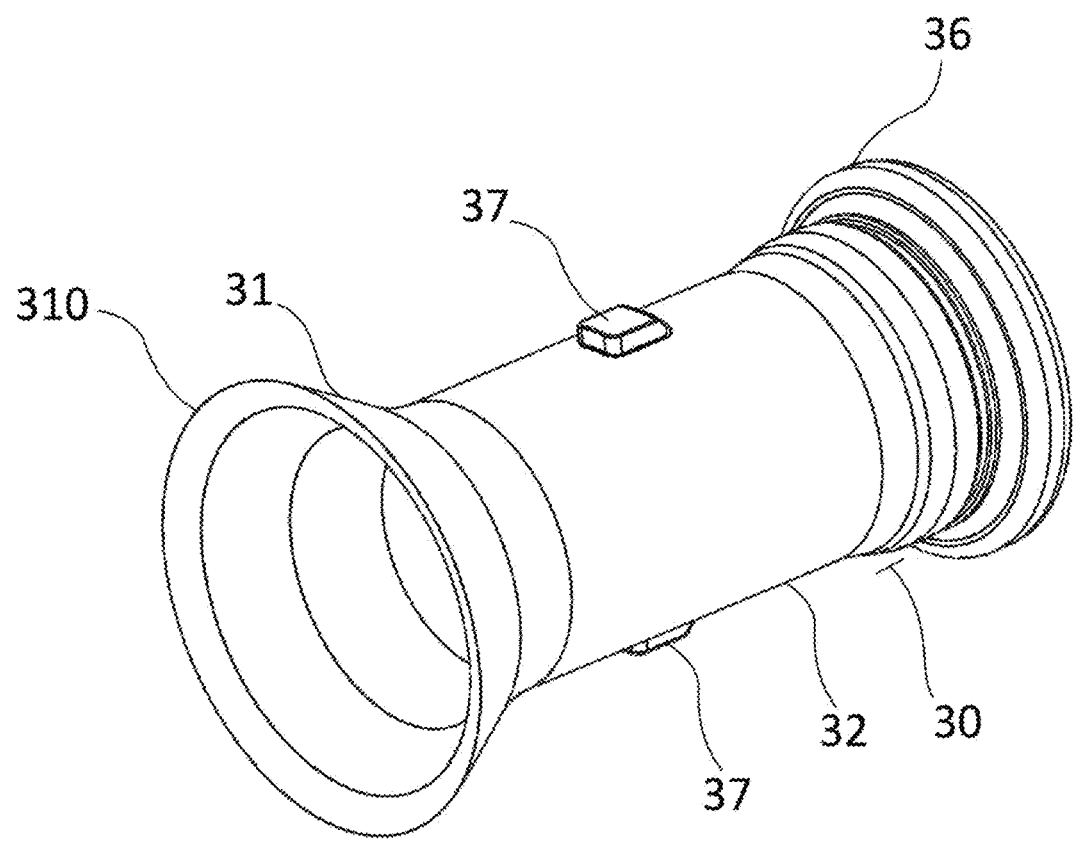
FIG. 4A is a perspective view of the flow cannula assembly. For clarity, the porous material attached on the outer surface of the flow cannula for tissue ingrowth is temporarily removed.

An embodiment of the flow cannula assembly 30A for connecting the EVBP 50 to a heart 20 is depicted in FIGS. 3 and 4A. In FIG. 3, which shows how the flow cannula 30 and the blood pump 50 is connected to left ventricle (LV), in which a sectional view depicting the artificially created flow passage and the interconnected cannula components inserted through a hole 21 cored in the ventricular wall. This flow cannula assembly 30A includes a bellmouth 31, a conduit body 32, a pair of male fastener 33 and female fastener 34, and a flange ramp 36. The bellmouth 31 is configured to be inserted into a heart chamber of the heart 20. The coupler 40 is configured to connect the flange ramp 36 of the flow cannula 30 to the inlet adapter 51 of the EVBP 50. The ramp surface 38 of the flange ramp 36 is connected to or in contact with the inlet adapter 51.

Figure 4B:
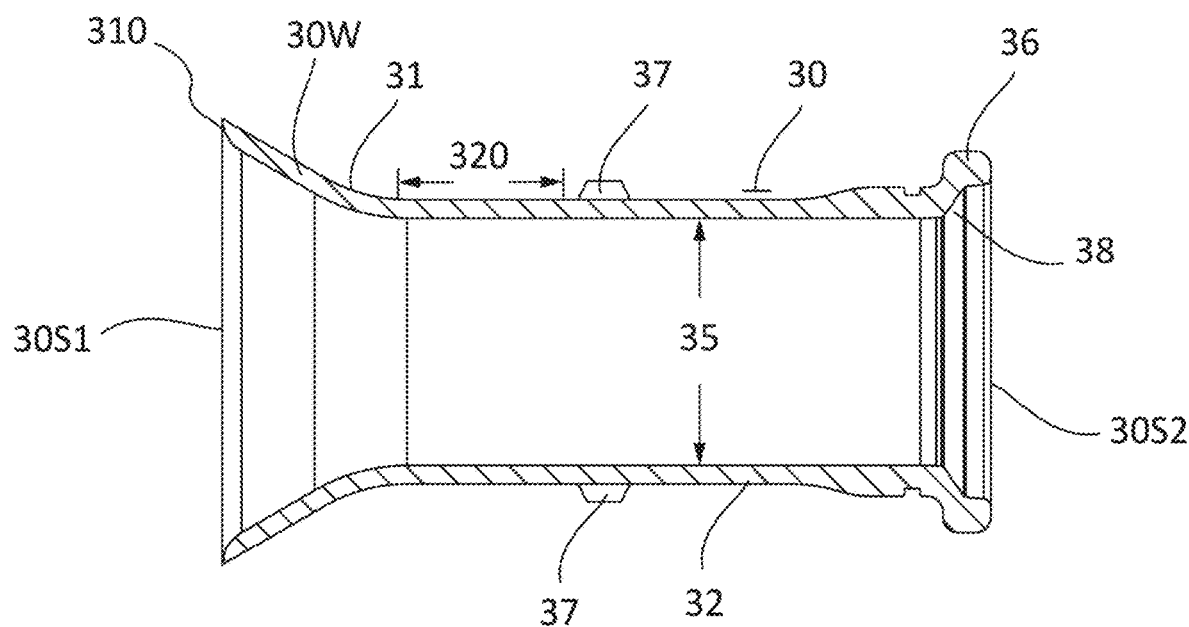
FIG. 4B is a cross-sectional view of the flow cannula shown in FIG. 4A.

Further shown in FIGS. 4A and 4B are the detail illustrations of the flow cannula 30. A distal orifice, defined as the farther cannula end viewed from the connected circulatory support system 10, is configured in a bellmouth shape with gradually increasing cone diameter. The cone angle of the bellmouth 31 is typically 30-75 degrees relative to the axis of revolution of the conduit body 32. The central portion of the flow cannula 30 is a straight conduit body 32 with a uniform cross-sectional configuration, wherein the conduit body 32 is curved or bendable. The cannula material is semi-rigid and flexible, which is usually constructed by mold injectable polymeric materials. The funnel-shaped flow cannula 30 constitutes a geometric locking mechanism when inserted across a cored through-hole 21 of the heart 20 (see FIG. 3) near the ventricular apex. At the second end 30S2, the blood-contacting inner surface of the flow cannula 30 is configured to have a smooth geometric transition to the inlet adapter 51 of the connected blood pump 50.

A surface portion 320 of the conduit body 32 in contact with the cored myocardium can be textured to promote tissue ingrowth during the wound healing period. The textured surface portion 320 can be made by attaching a fabric material with appropriate porosity or by depositing a thin layer of polymeric filaments generated, for example, by electrospinning. This textured surface portion 320 can help adherence or seal the implanted flow cannula 30 via tissue ingrowth and hence maintain postoperatively the long-term hemostasis property required for a safe implant.

Figure 5:
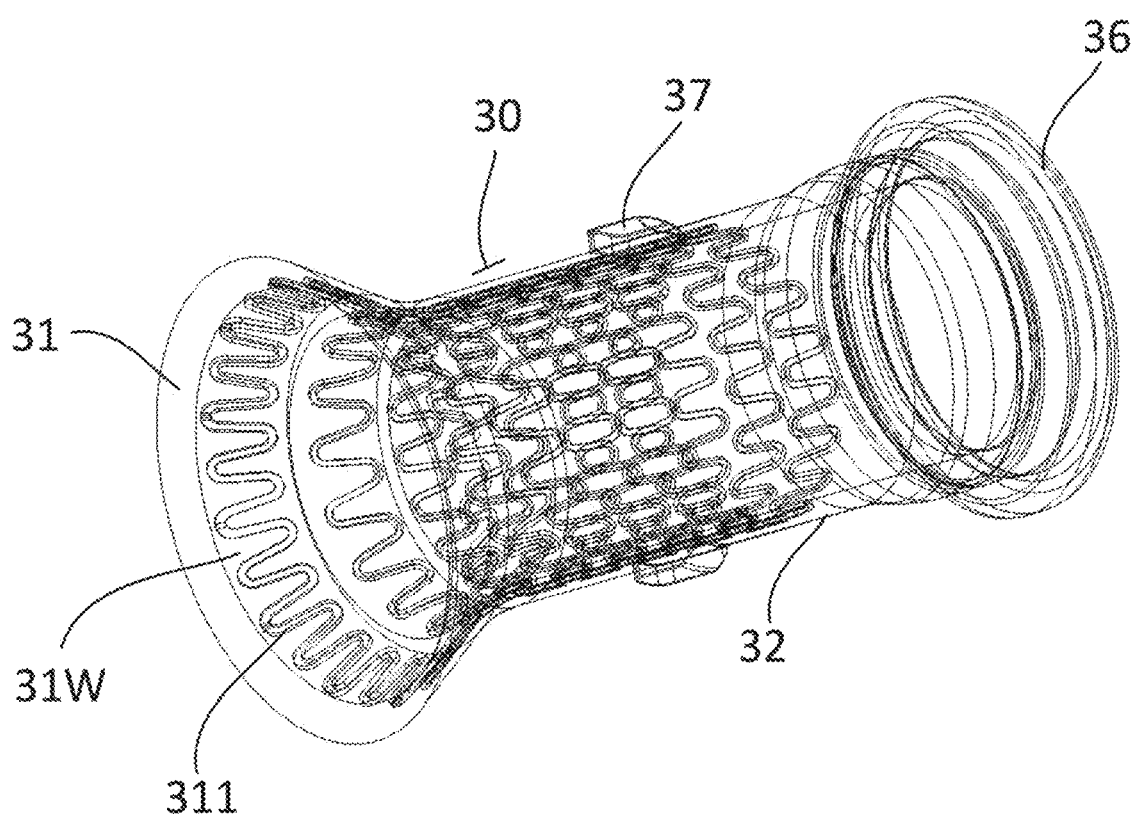
FIG. 5 is a perspective, transparent view of a Nitinol stent reinforcement embedded in the flow cannula as another embodiment of the present invention.

Two embodiments of the aforementioned funnel-shaped cannula are shown in FIGS. 4A, 4B, and FIG. 5, respectively. For these embodiments, polymeric elastomer such as silicone or polyurethane can be adopted as the material, which can be mold casted or injected into a seamless cannula with smooth blood-contacting surface. At the distal end of the bellmouth 31 is a sharp-edged tip 310 that can be attached to the endocardium with minimal geometric discontinuity. In addition, because the wall around the tip end is gradually thinned, the rigidity of the bellmouth 31 reduces in proportion to the wall thickness toward the tip, rendering the bellmouth 31 flexible and shape-conformal when compressed against the endocardium.

Another embodiment is to have the previous embodiment (FIGS. 4A and 4B) embedded with a metallic stent 311 (such as a Nitinol stent reinforcement), as shown in FIG. 5. The stent 311 is embedded inside the cannula wall 30W of the flow cannula 30. In particular, the stent 311 is inside the conduit body 32 and the bellmouth 31 to provide stiffness. By embedding the stent 311 inside the cannula wall 30W, the cannula wall thickness can be further thinned to decrease the outer conduit diameter. Hence, the implantability of the stent embedded cannula 30 would be upgraded without compromising the hemodynamic performance which is dominated by the inner diameter 35. Moreover, in some embodiments, the stent 311 made by Nitinol reinforcement may share a substantial amount of the pulsatile pressure loading exerted on the conduit body 32, hence enhancing the conduit durability and safety. In general, super-elastic Nitinol stent is preferred because of its ability to endure large deformation without structural yielding that meets the foldability requirement of the present cannula.

Figure 6A:
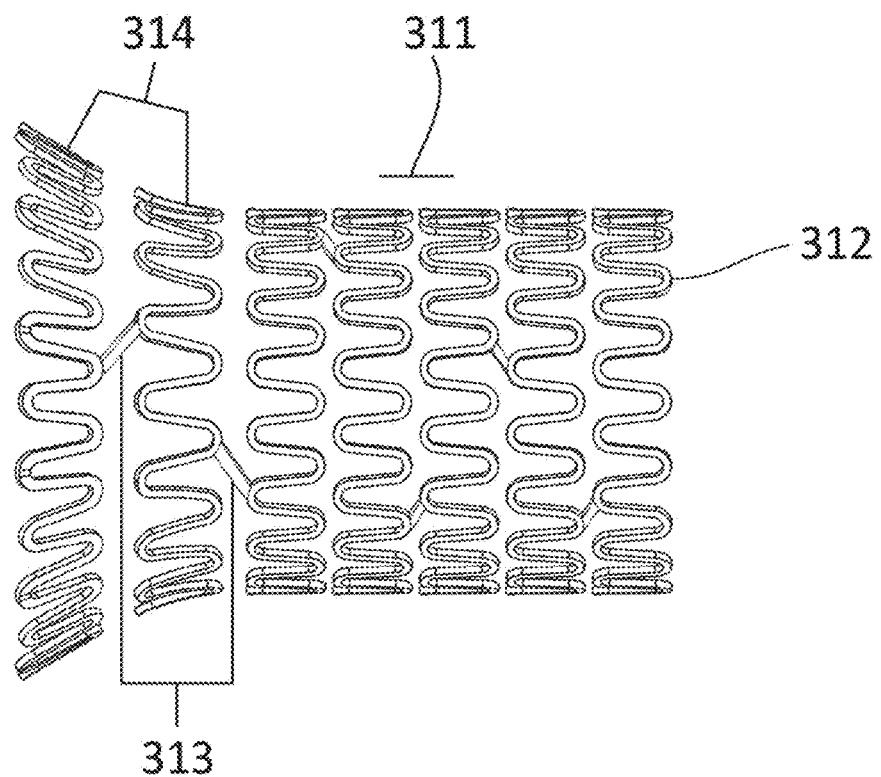
FIG. 6A shows a lateral view of a Nitinol stent embedment of FIG. 5.
Figure 6B:
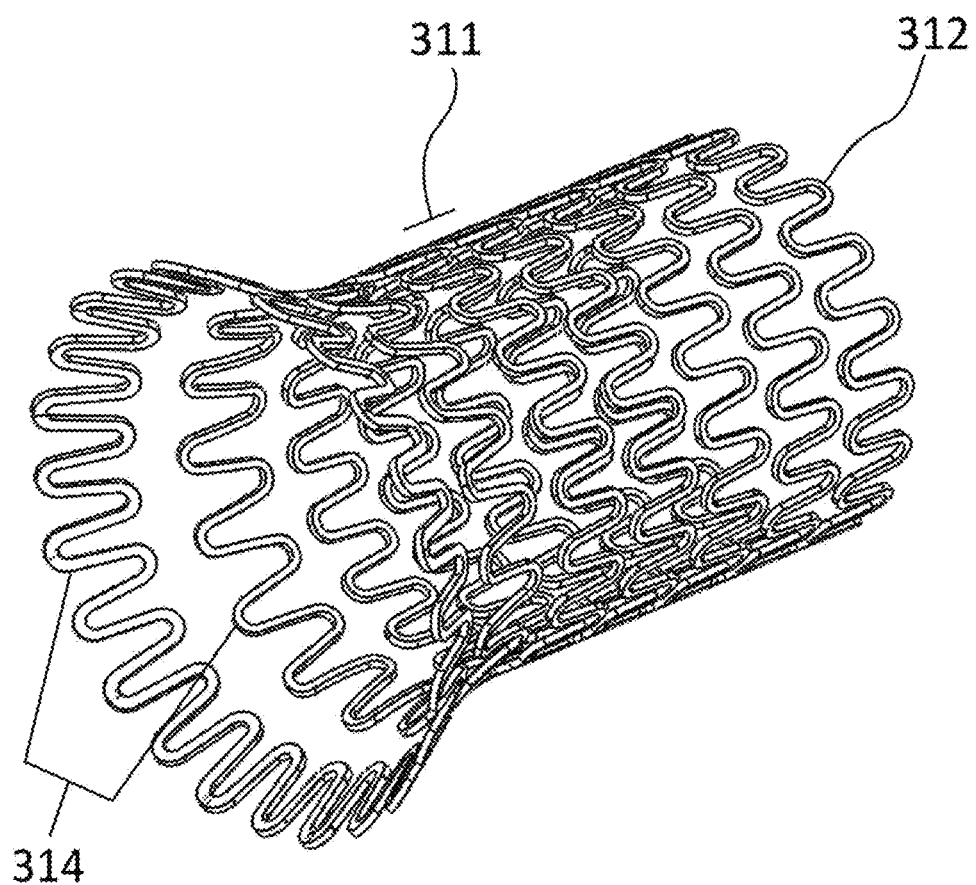
FIG. 6B shows a perspective view of a Nitinol stent embedment of FIG. 5.

A lateral and perspective view of a representative stent 311 insert is illustrated in FIG. 6A and FIG. 6B, respectively. The array of zig-zag rings 312 is responsible for resisting the radial load whereas the connecting portion 313 clusters the rings 312 together to resist the axial force. Several cone-shaped stent rings 314 are embedded in the wall of bellmouth 31. For a thin-walled bellmouth 31 the radial strength is gradually weakened along with the increase of the cone diameter toward the tip 310. The wall thickness of the bellmouth 31 tapers toward the tip 310. Notice that when the bellmouth 31 is locked with female fastener 34, insufficient radial strength in the bellmouth 31 may lead to local structural buckling and loss of shape-conformality, resulting in massive bleeding out around the buckled tip 310. The Nitinol stent reinforcement 311 can improve the stiffness of this polymeric material by providing sufficient anti-buckling capability without a need to increase the wall thickness of the bellmouth 31.

Referring to FIG. 3 again, prior to the flow cannula 30 insertion, a through-hole 21 in the range of 10-15 mm in diameter, is required, which is intentionally kept smaller than the outer diameter of the inserted conduit body 32. Deformability of the present cannula invention is hence essential, which allows the bellmouth 31 and flow cannula 30 to be crimped into a much smaller prepacked form to facilitate insertion. Following the bellmouth 31 insertion and release of crimping constraint, the folded cannula 30 will resume its original form and diameter, and expand snuggly against the cut surface of the undersized cored myocardial through-hole 21. Similarly, the intake of the bellmouth 31, after being freed from crimping constraint, will expand and hence constitute an anti-dislodging anchorage against the cored endocardium.

Surgical implantation of LVAD has been routinely using LV apex as a connection location. The cored hole size (10-15 mm in diameter) required for the present cannula implant 30 can be substantially smaller when compared to that of a rigid-walled inflow conduit (20-30 mm in diameter) pertaining to the contemporary rotary blood pumps. Excising lesser amount of tissue mass from the cardiac wall is surgically and anatomically advantageous. It not only reduces a permanent loss of contractile muscle, but also mitigates the risk of injury to papillary muscle and chordae tendineae that are responsible for atrioventricular valvular function. Notice that mitral valve regurgitation would lead to pulmonary congestion and hypertension, causing pulmonary edema and death-threatening right heart failure. Coring-induced chordae tendineae and papillary muscle injury should be avoided, and a smaller cored hole can significantly reduce this surgical risk as well as the resultant pulmonary complications. Furthermore, it would fractionally increase the restricted internal diameter of the LV commonly encountered in HFpEF, thus reducing the possibility of cannula tip obstruction during pump fill (or LV "suck-down").

Unlike the existing inflow cannula attachment designs that commonly require 10-12 suture stitch pairs, circumferentially sewn around the cored myocardial hole 21, to attach a LVAD onto a heart 20, the present invention innovates a sutureless fixation approach. Conventional suture fixation relies on the tension force generated in the suture string by pulling tight the opposingly anchored suture pair. In a sharp contrast, the present sutureless pump attachment adopts a completely different fixation force generation method provided by the fastener pair 33, 34. This new attachment design locks together and anchors the bellmouth of the flow cannula 30 circumferentially onto the connection site myocardium.

The detailed structure of the male and female fasteners 33, 34 are shown in FIGS. 7A-7B and FIGS. 8A-8C, respectively. FIG. 9 shows the integrated fasteners 33, 34 as mounted on the flow cannula 30. When mounting these fasteners 33, 34 onto the cannula body 32, the deformability ability of the cannula is required as a prerequisite. The flange ramp 36 (at the second end 30S2) of the flow cannula 30 ought to be compressed or folded into a smaller crimped profile to pass through the fasteners 33, 34 sequentially. Upon the release of the crimped profile of flow cannula 30, the male fastener 33 is first mounted and seated onto the conduit body 32 via an engagement of the multiple (two) through slots 330 with the multiple (two) protruded seats 37 protruded outside of the wall of the conduit body 32. In some embodiments, two protruded seats 37 are located on the opposite sides of the conduit body 32. The female fastener 34 is inserted following the same crimping and release of the flange ramp 36 and then screwed onto the male counterpart 33. The female fastener 34 is then advanced forward until in contact with the epicardium. Suitable compression force required for device fixation and leakage seal can be applied and the locking tightness is determined by the surgeon or controlled by a torque wrench.

Figure 7A:
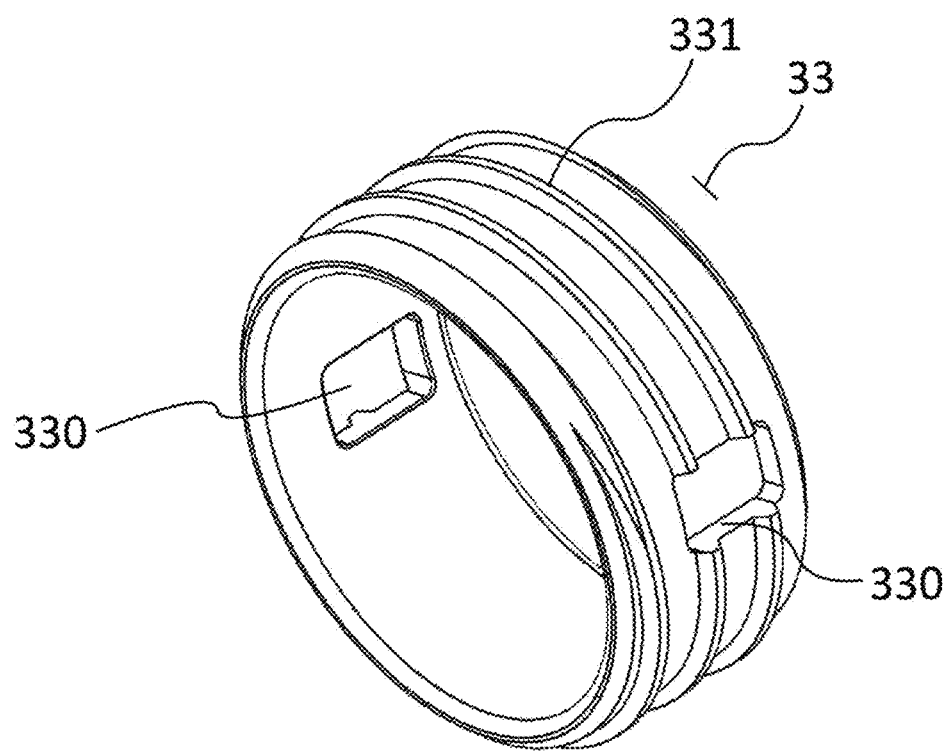
FIG. 7A is a perspective view of the male fastener component shown in FIG. 3.
Figure 7B:
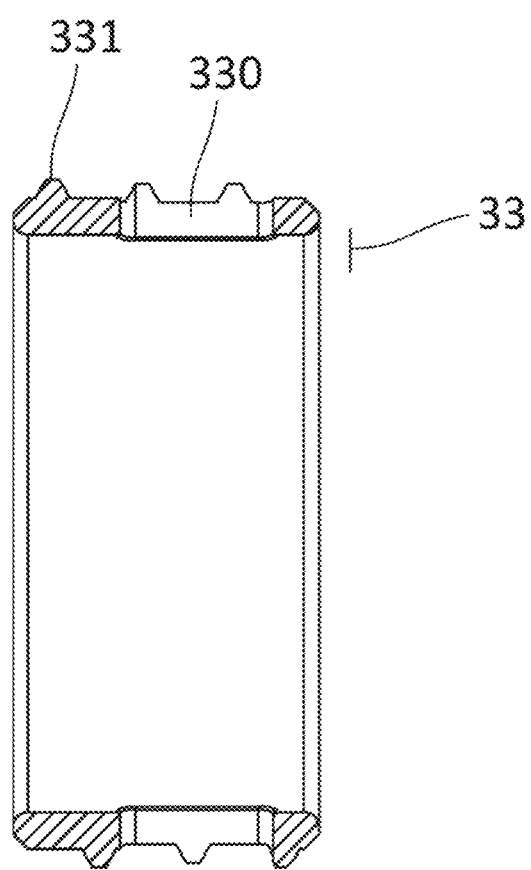
FIG. 7B is a sectional view of the male fastener component shown in FIG. 3.

Depicted in FIGS. 7A and 7B are the perspective and sectional views of the male fastener 33. Screw threads 331 are carved on the external surface of the male fastener 33, from end to end, with multiple through slots 330 located approximately around the middle region of the male fastener 33. The inner diameter of the male fastener 33 is substantially equal, with a small clearance, to the outer diameter of the cannula conduit body 32. When mounted onto the cannula 30, the protruded seats 37 on the conduit body will interlock with the through slots 330 and thereby work as anchor supports to provide counteracting axial and lateral forces required for screw locking with the female fastener 34.

Figure 8A:
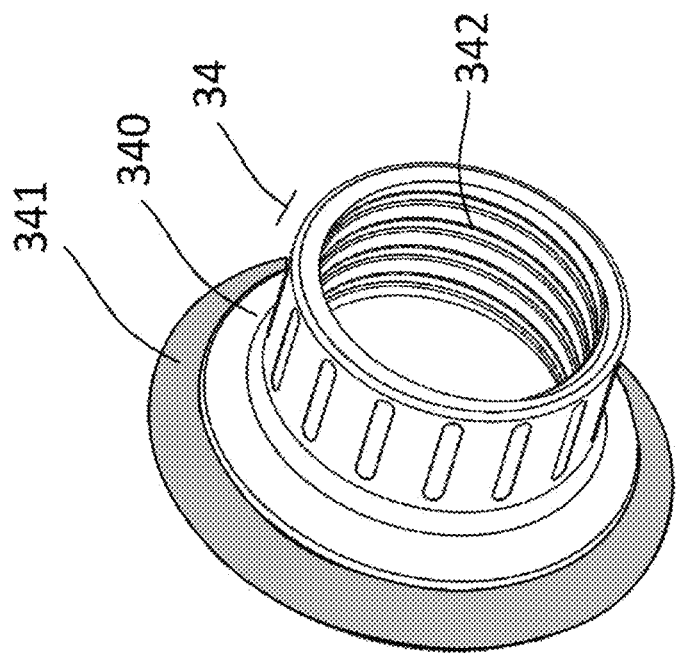
FIG. 8A is a perspective (frontal and rear) view of the female fastener component shown in FIG. 3.
Figure 8A:
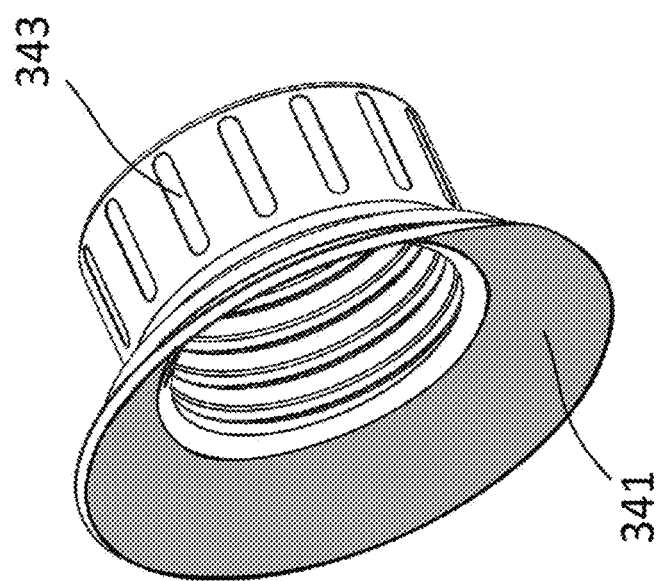
Figure 8B:
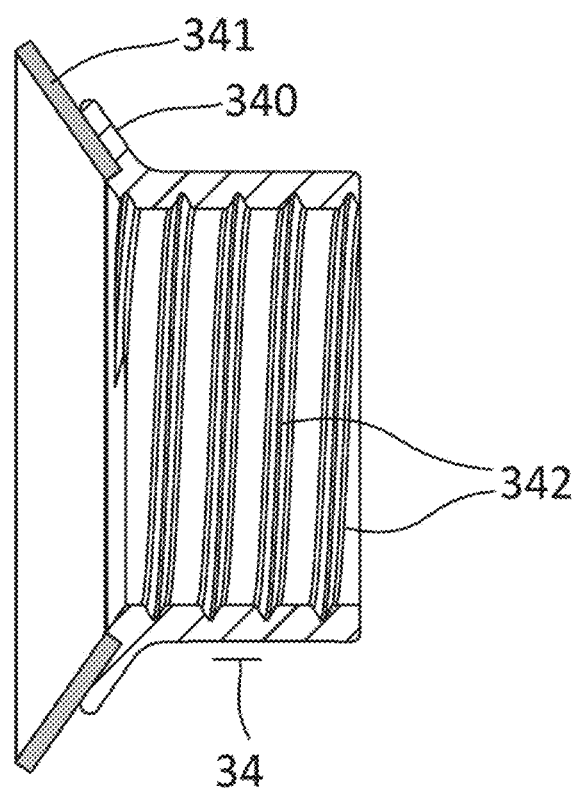
FIG. 8B is a sectional view of the female fastener component shown in FIG. 3.
Figure 9:
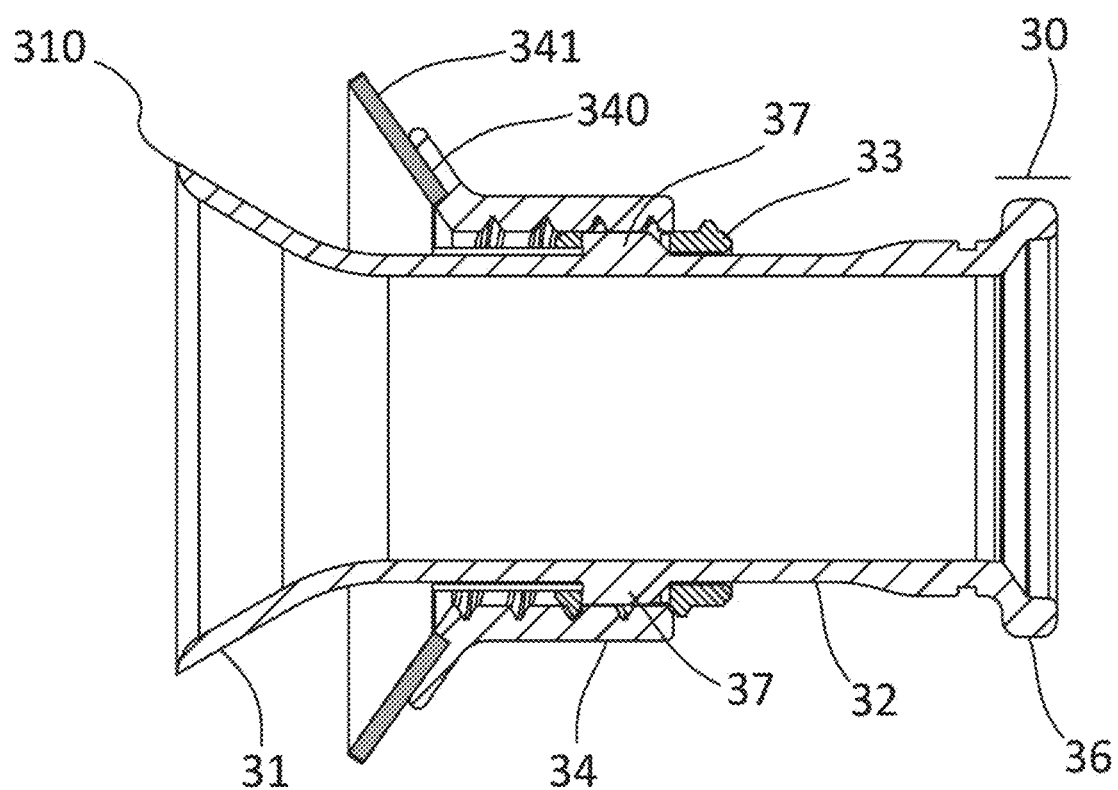
FIG. 9 is a sectional view of an integrated fastener pair in locking position with respect to the bellmouth and conduit body of an embodiment shown in FIG. 3. Note that porous material attached on the outside surface of the flow cannula for tissue ingrowth is not shown for clarity.

The embodiments of female fastener 34 are illustrated in FIGS. 8A, 8B, as well as in 8C and 8D, respectively. The female fastener 34 is a lock nut having a funnel-shaped distal cap (female fastener cap) 340 to be compressed against the epicardium for locking and seal purposes. The cap angle of the cap 340 corresponds to the bellmouth angle of the bellmouth 31. As the screws of male and female fasteners 33, 34 are tightened together, compression force will be evenly distributed in the sandwiched myocardium between the cap 340 and the bellmouth 31. Moreover, the cone of bellmouth 31 will deform, in compliance with the fitted endocardium terrain, to simultaneously achieve the functions of bleeding prevention and pump fixation. The cap 340 has a cushion cuff 341 (configured for contact with the epicardium), which is around and attached the outer rim of the cap 340. In some embodiments, the cushion cuff 341 is made of a surgical felt. The thread 342 is to be matched with its counterpart 331 on the male fastener 33. A number of knurled recesses 343 are made around the external body of the female fastener 34 for an easy exertion of screwing torque.

Figure 8C:
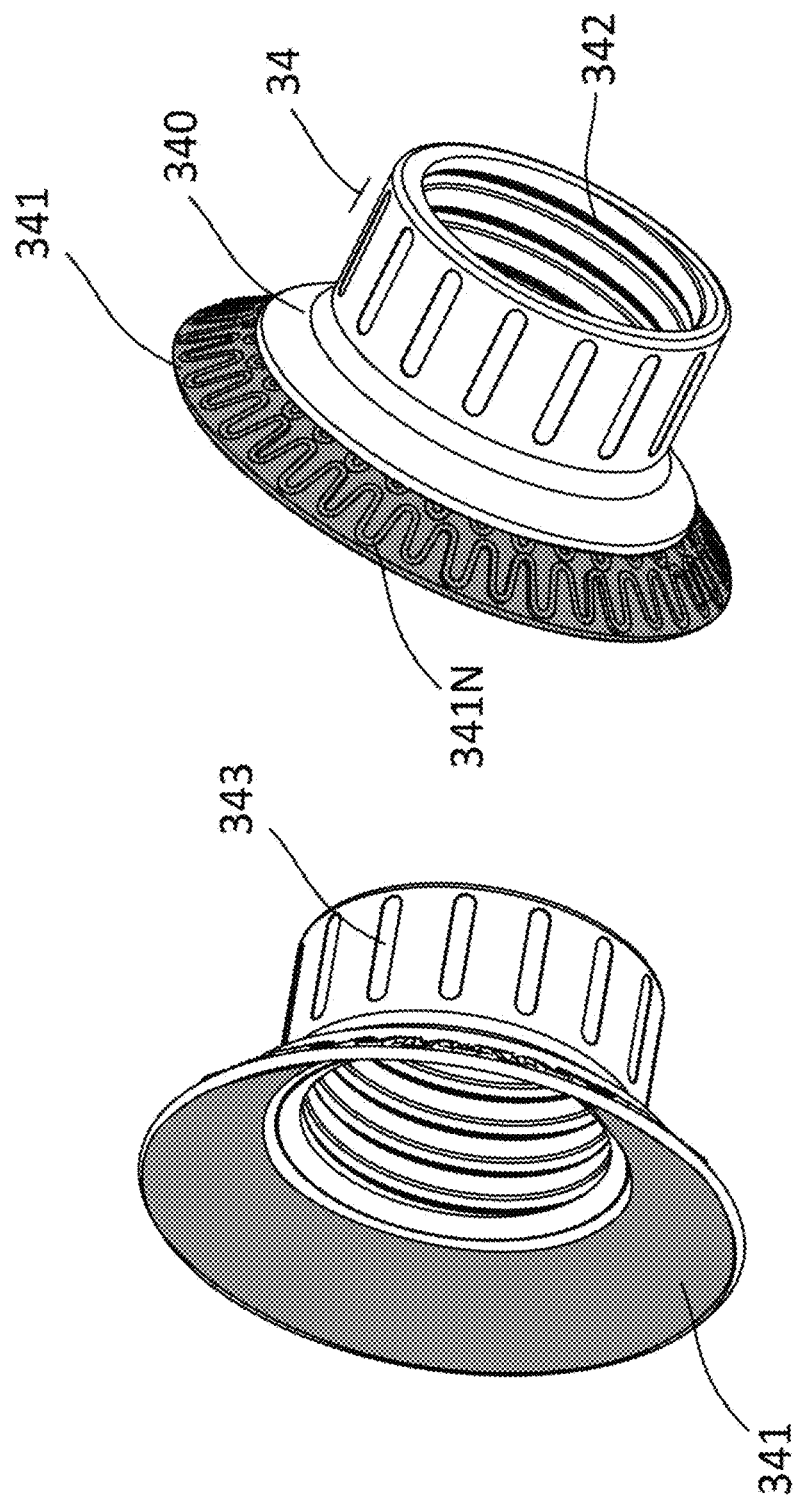
FIG. 8C shows a variant of the female fastener design depicted in FIG. 8A, of which the cuff is additionally supported by a Nitinol stent.
Figure 8D:
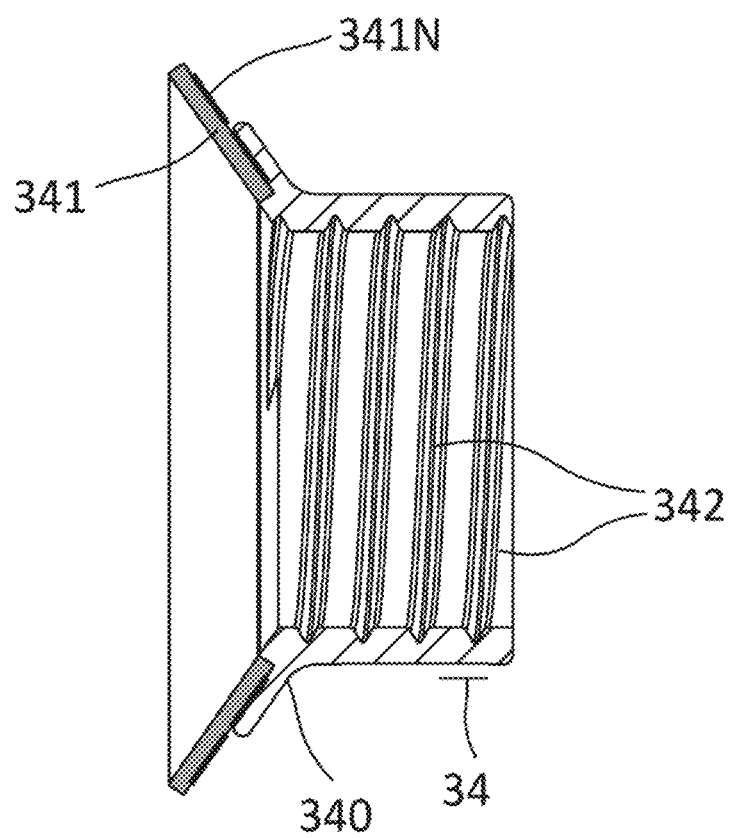
FIG. 8D shows a variant of the female fastener design depicted in FIG. 8B, of which the cuff is additionally supported by a Nitinol stent.

The present sutureless flow cannula implantation may encounter postoperative tissue atrophy at the clamped connection site. Such tissue atrophy will jeopardize the seal effectiveness and potentially causes bleeding at the connection site. In FIGS. 8C and 8D are shown another embodiment of the female fastener 34 intended to mitigate this atrophy-induced postoperative bleeding. The cuff 341 is additionally supported by a cone-shaped Nitinol stent 341N similar to that of the bellmouth 313, 314 illustrated in FIGS. 6A and 6B. As the female fastener 34 is compressed onto the epicardium, the deformed super-elastic Nitinol stent 341N will provide a contact spring load to assure that the cuff 341 always adheres to the epicardium during the wound healing process, hence obviating the risk of postoperative atrophy-induced blood leak.

Mechanically, by screw tightening the male and female fasteners 33, 34, the bellmouth 31 and the cap 340 of the female fastener 34 clamp the sandwiched myocardium from both sides of the cored hole 21 of the heart 20 to accomplish the fixation and leak-free requirements. It is worth noticing that the bellmouth 31 is shape-conformal to endocardium when compressed. The semi-rigid bellmouth 31 can adaptively fit itself against the endocardial terrain, forming a seal barrier to obviate blood leak concern. The male fastener 33 is anchored on the protruded seat 37 of the conduit body 32, working as a base to counteract the screwing locking force generated. A cone-shaped felt cuff 341 is attached with the cap 340, which, when locked, provides a non-traumatic cushion between the cap 340 and the contacted epicardium. The soft-contact feature provided by felt cushion is another guarantee of hemostasis. Tissues or cells grow inward into the cuff material 341 along with the postoperative wound healing process. The cuff 341 can thus work as a long-term fixation mechanism for immobilizing the implanted flow cannula 30. Moreover, a couple of stay sutures can be sewn around the cuff 341 to prevent unscrew of the female fastener 34.

Forces and strain involved in cannula deformation confers a special design feature of the present invention. Material elasticity consideration, in fact, needs to be carefully incorporated in the present design. Functionally, the foldability of the flow cannula 30 allows the cannula to be crimped into a smaller diameter for bellmouth 31 insertion and fasteners 33, 34 mounting, which forms a foundation for achieving the present sutureless screw locking invention.

It is worth mentioning that the embodiment of the sutureless attachment possesses a built-in positive feedback mechanism for improving the seal against the heart. During systole, the LV chamber pressure is elevated and further augmented by co-pulsatile pumping assistance, increasing the compression force on the bellmouth 31 pushing it onto the sloping heart muscle surface which will better seal around the attached flow cannula 30. The chance of bleeding even during systemic hypertension is virtually eliminated by this design feature. This positive feedback effect, namely the larger the LV pressure the better the seal effectiveness that is provided by the bellmouth 31, is lacking in the conventional device fixation by means of suturing. Compression type locking mechanism enables a distributed force to be exerted around the clamped myocardial area in contact. The soft contact nature over bellmouth 31 and female fastener cap 340 averts the conventional concentrated string cutting force generated within myocardium, which, could lead to bleeding through enlarged suture fissure at hypertension. Cardiac muscle is particularly vulnerable to string cutting associated with conventional suturing anastomosis, a problem that is variably dependent on the suturing skills of the individual surgeon.

The present epi-ventricular assist device is operated in a co-pulsatile manner with respect to the native heartbeat. During LV systole the intraventricular pressure and the systolic arterial blood pressure will both be raised owing to the co-pulsatile pumping support. This support characteristic is vastly different from the situation with rotary blood pump operation which decreases LV pressure during support. Such device-induced hypertension demands a far superior seal around the ventricular cannulation site and calls for particular attention in designing a flow cannula for a co-pulsatile assist device.

Figure 10A:
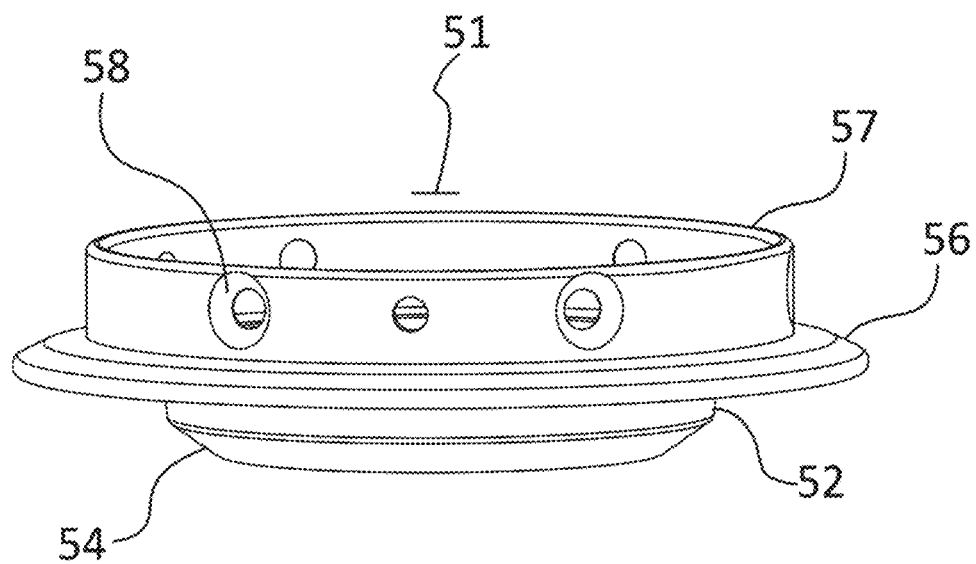
FIG. 10A is a perspective view of a blood pump inlet adapter pertinent to connect with the present flow cannula.
Figure 10B:
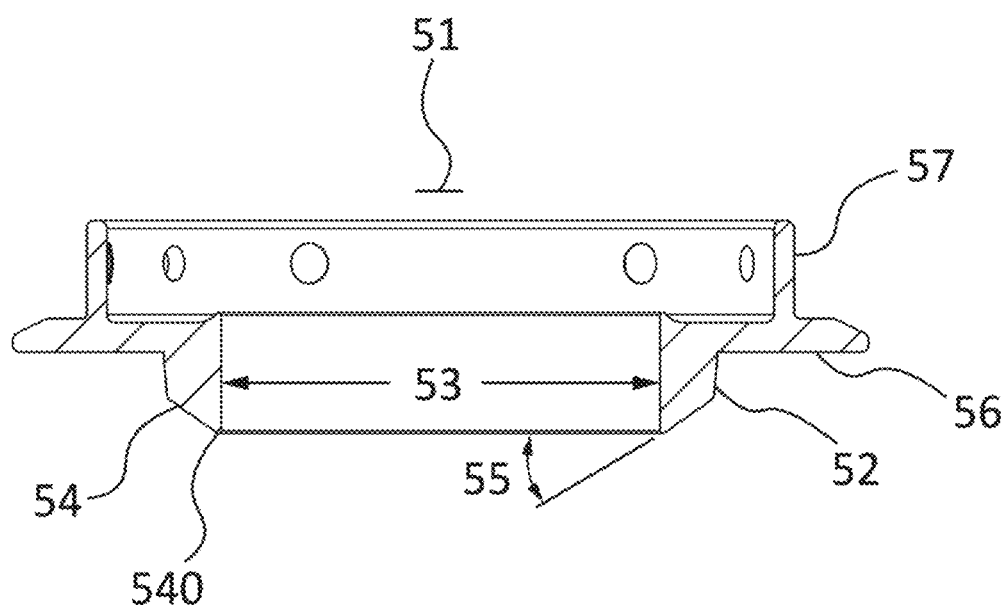
FIG. 10B is a sectional view of a blood pump inlet adapter pertinent to connect with the present flow cannula.

As shown in FIGS. 10A and 10B, the inlet adapter 51 of the connected blood pump 50 has the beak flange 56 and the adapter body 57. The beak flange 56 has a beak 52 that has an inner diameter 53 slightly larger than the inner diameter 35 of the conduit body 32 (FIG. 4B). To enhance the fault tolerance associated with step discontinuity generated at interface, the present surface of the joint 54 of the beak 52 is ramped with an inclination angle 55 to the stream direction (or the contact plane). In some embodiments, the angle has a range of 30-60 degrees. Such ramp interface design averts step or gap being generated at the joint due to limited manufacturing precision or matching concentricity associated with conventional butt connection. The adapter body 57 has multiple eyelets 58 which are equipped for joining the inlet adapter 51 with the blood pump 50.

Figure 11A:
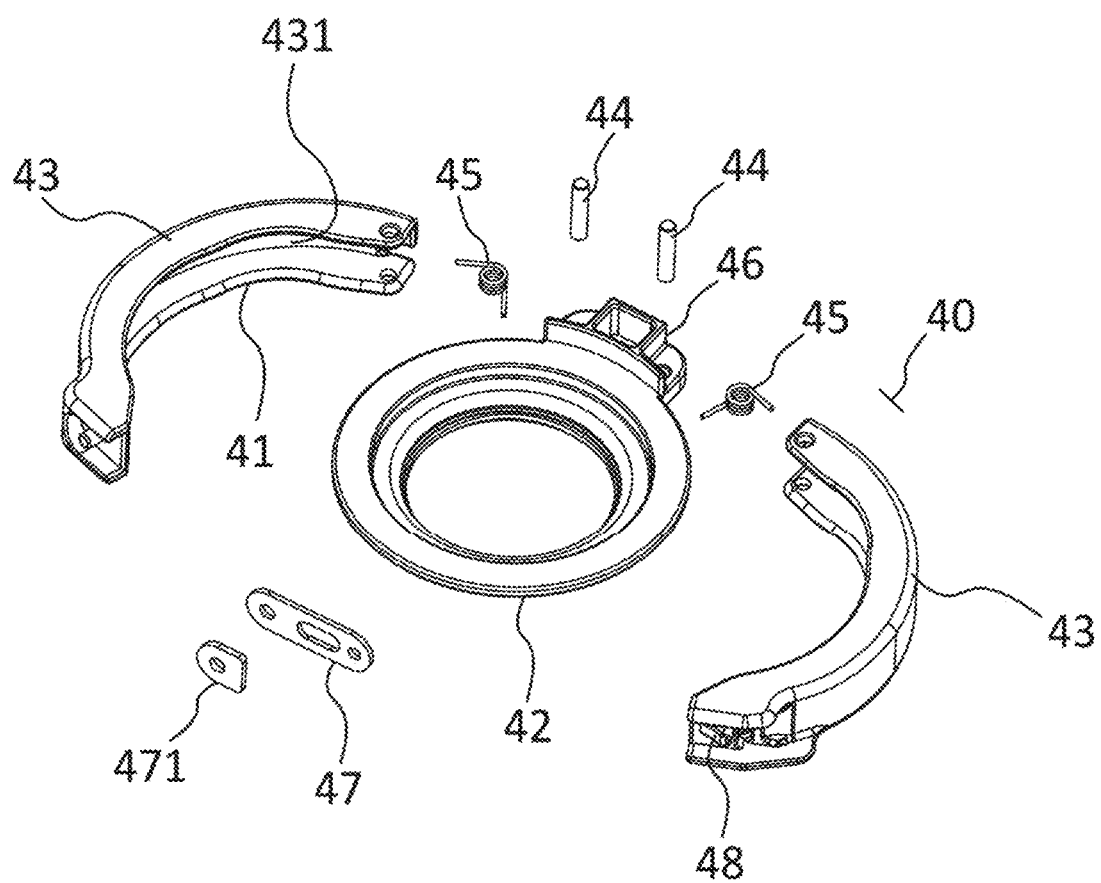
FIG. 11A is an exploded view showing the components of the coupler.
Figure 11B:
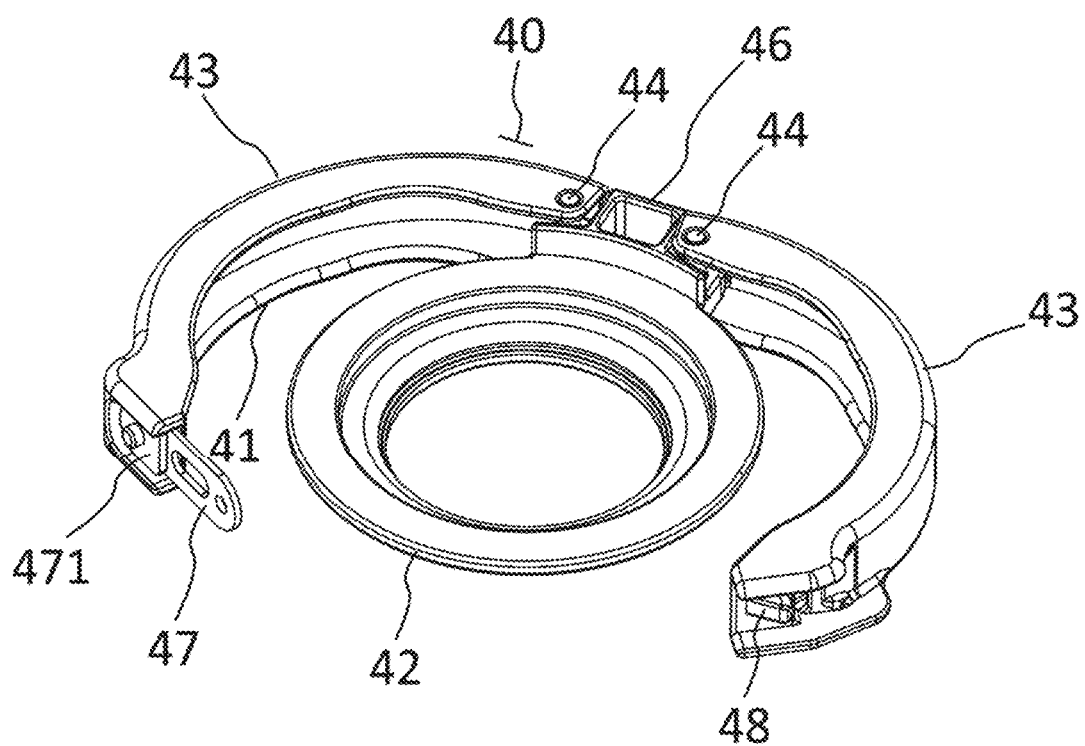
FIG. 11B is a perspective view of the coupler in an unlatched open state.
Figure 11C:
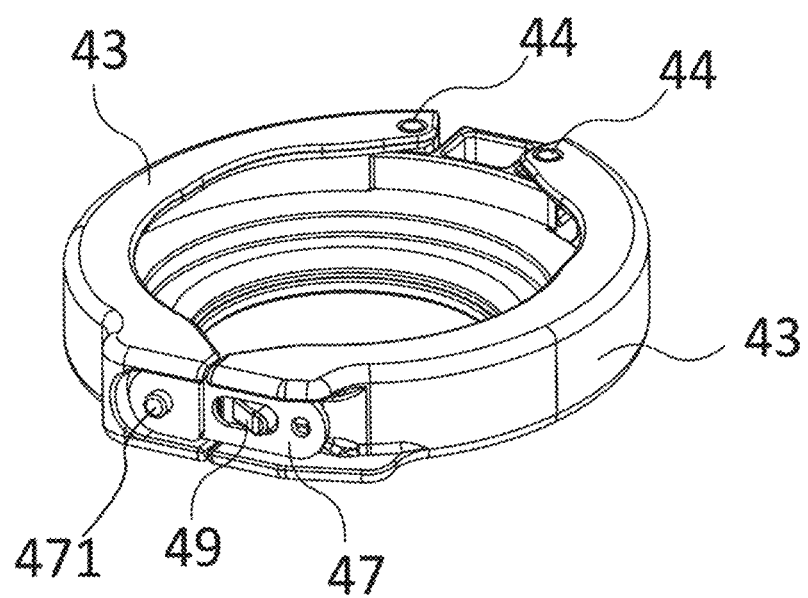
FIG. 11C is a perspective view of the coupler in a locked form with latch closed.

FIGS. 11A to 11C show the detailed structure of the coupler 40, which is designed herein to connect the flange ramp 36 with the pump inlet adapter 51.

FIG. 11A is an exploded view of the components of the coupler 40 that integrate together the flow cannula 30 and the blood pump 50. The coupler 40 includes a flange base 42, a pair of collars 43, and hinges (or a hinge assembly) 44 that join together the collars 43 with the flange base 42. Spring coils (or a spring coil assembly) 45 are loaded in a hinge joint 46, maintaining the collars 43 in an open position when unlocked (FIG. 11B). The locking mechanism is an anti-decoupling latch 47, made of slotted leaf spring and fixed by a slab 471 welded to one of the ends of the collars 43. The flange base 42 has a substantially circular-shaped structure, and each collar 43 has an arc-shaped structure. The hinge joint 46 is located at the side of flange base 42, and the collars 43 are pivotally connected to the hinge joint 46 and rotatable to the hinge joint 46 and the flange base 42. The internal grooved slot 431 of the collars 43 is configured to receive the flange base 42, the flange ramp 36 of the flow cannula 30, and the beak flange 56 of the inlet adapter 30 (described later).

A concentric coupling of flow cannula 30 with blood pump 50 will minimize the interface discontinuities which is important for generating a thromboresistant coupling. In some embodiments, for coupler 40 to concentrically connect to the rigid beak 52 with the semi-rigid cannula flange ramp 36, a simultaneous catching of the collar 43 around the entire peripheral rim of flange base 42 is critical. In other words, the collar contour 41 of the collar 43 plays an essential role in accomplishing such simultaneous catching. The reasons why errors would be incurred during coupling and how remedy can be applied to rectify such coupling errors and the resultant risk of clot formation are explained in the referenced disclosure U.S. application No. 63/162,098.

Quick-connection type locking can easily be carried out by closing the collars 43 that will be latched without unintentional unlocking, as depicted in FIG. 11C. A leaf spring type latch 47 is installed at the tip of one collar 43, fixed by welding with a slab 471. This said latch 47 will be bent as it slides on a ramp 48 on the opposing collar in the course of locking. As said latch 47 clears the top of the ramp 48, it will drop down to the base of said ramp 48 by elastic restoring force, working as a safety catch to prevent accidental latch unlock or collar opening caused by pump vibration or rocking in long-term use. For pump explant or exchange that requires component decoupling, the latch 47 can be bent and lifted upward by a special tool, permitting an unlocking force to be exerted to rotationally open the collars 43 and hence disengage the blood pump 50 from the cannula 30.

Such interface connection between pump and cannula described above has two hemodynamic merits for reducing thrombus formation in-situ. First, there will be literally no obvious step or gap type joint discontinuities generated as observed in the conventional butt connection. Second, flow stasis located at the interface of the beak leading-edge 540 (FIG. 10B) of the joint 54 can be minimized. Hence, blood stream flowing over the connection interface will be maintained with high-speed, substantially superior to the butt connection with either forward- or backward-facing step at the interface that predisposes to flow stasis and promotes thrombus formation in-situ.

Numerous displacement type, pneumatically driven blood pump bodies can be mounted with the inlet adapter 51 disclosed herein to connect with the present flow cannula invention. Comparing to the prior arts of displacement type pumps without long-term implantable sensors, the present EVBP invention particularly requires a long-term reliable sensor system that can continuously track the heart rhythm. In order to facilitate co-pulsatile pumping, signals that can sense ventricular contraction and relaxation is required for pumping control. Either electrocardiogram (ECG) or ventricular pressure waveforms can be used as the reference signal to reflect the heart rhythm. Since a great percentage (30-40%) of advanced heart failure patients suffer from arrhythmia, pumping control based on ECG waveform meets with practical difficulty in application. Pressure-based pumping control, hence, is more advantageous, albeit the trigger detection algorithm is more complex to design.

Figure 12:
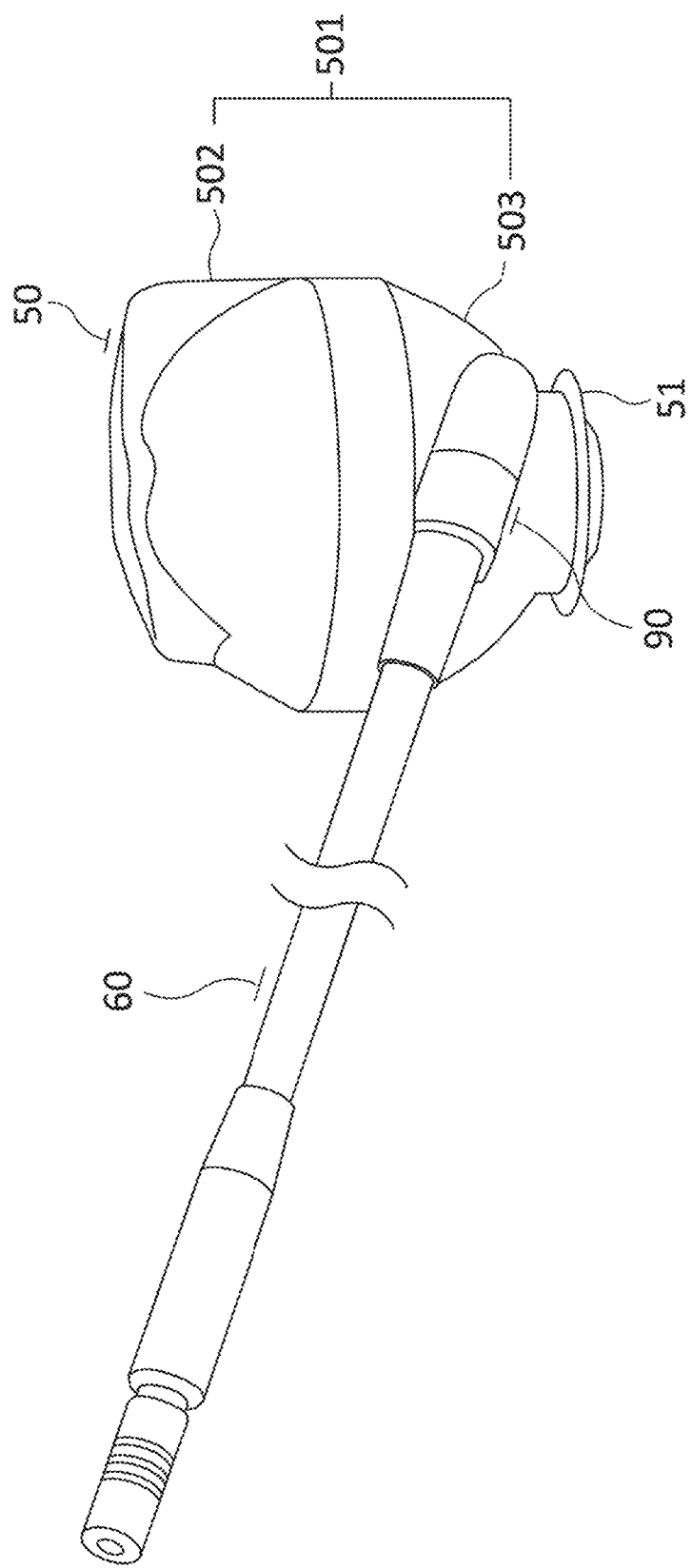
FIG. 12 is a perspective view of a preferred embodiment of a displacement type blood pump suitable for use in the epi-ventricular assist device system disclosed in FIG. 3.
Figure 13:
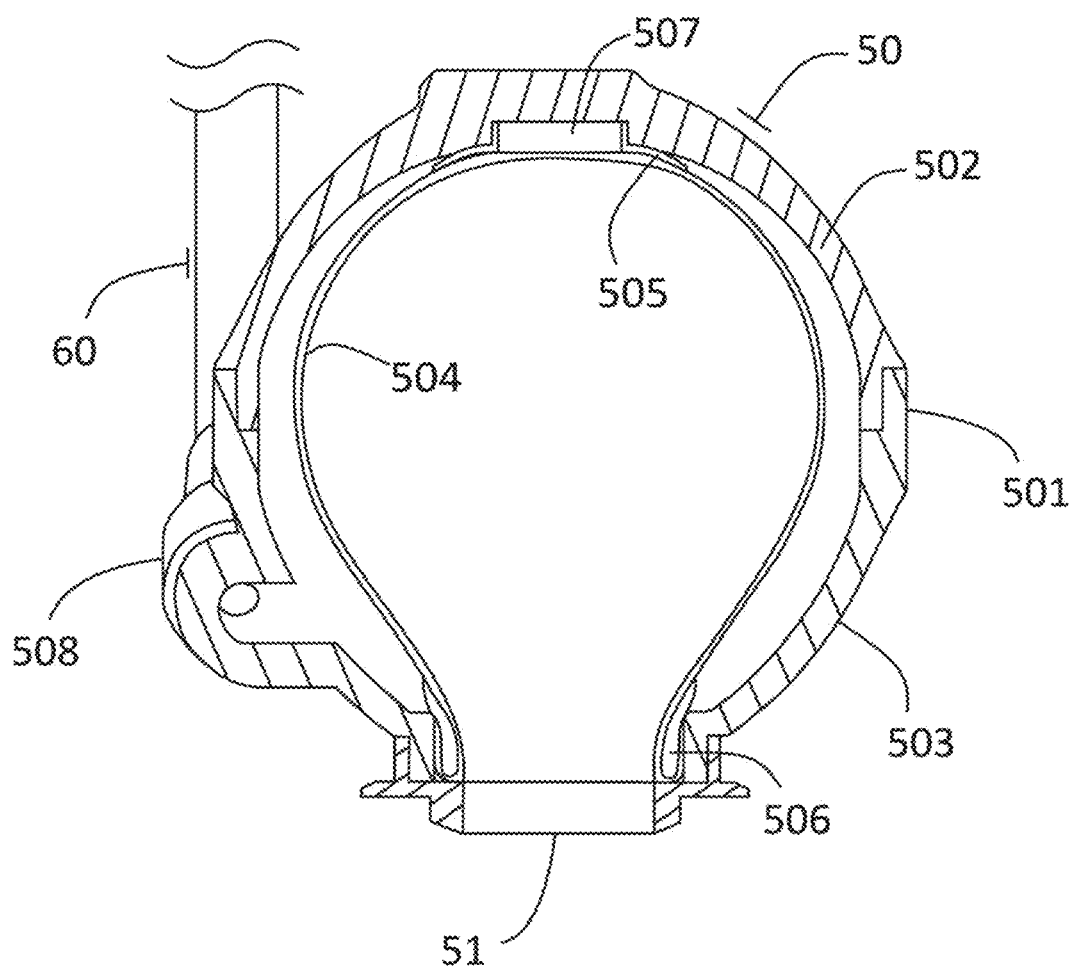
FIG. 13 is a sectional view of a preferred embodiment of a displacement type blood pump suitable for use in the epi-ventricular assist device system disclosed in FIG. 3.

An exemplary embodiment of the blood pump 50 is a pressure sensor-embedded valveless displacement pump, as illustrated in FIGS. 12 and 13. This EVBP 50 includes a rigid housing (blood pump housing) 501, a blood sac 504, a stem suspension (such as including a pair of axi-symmetric stems 505, 506) suspending the sac 504 with the housing 501, and a sensor or a miniature pressure sensor (assembly) 507 embedded in the proximal shell 502 of the pump housing 501 to represent a heart rhythm. Further, the inlet adapter 51 is equipped at the distal end of the blood pump 50. A distal driveline (or percutaneous lead) 60 is also included to incorporate pneumatic power transport and pressure signal transmission between the blood pump 50 and the external driver 70. The distal driveline 60 is connected with the distal shell 503 via a feedthrough 508. In some embodiments, the stem suspension (stems 505, 506) can be asymmetric.

Figure 14:
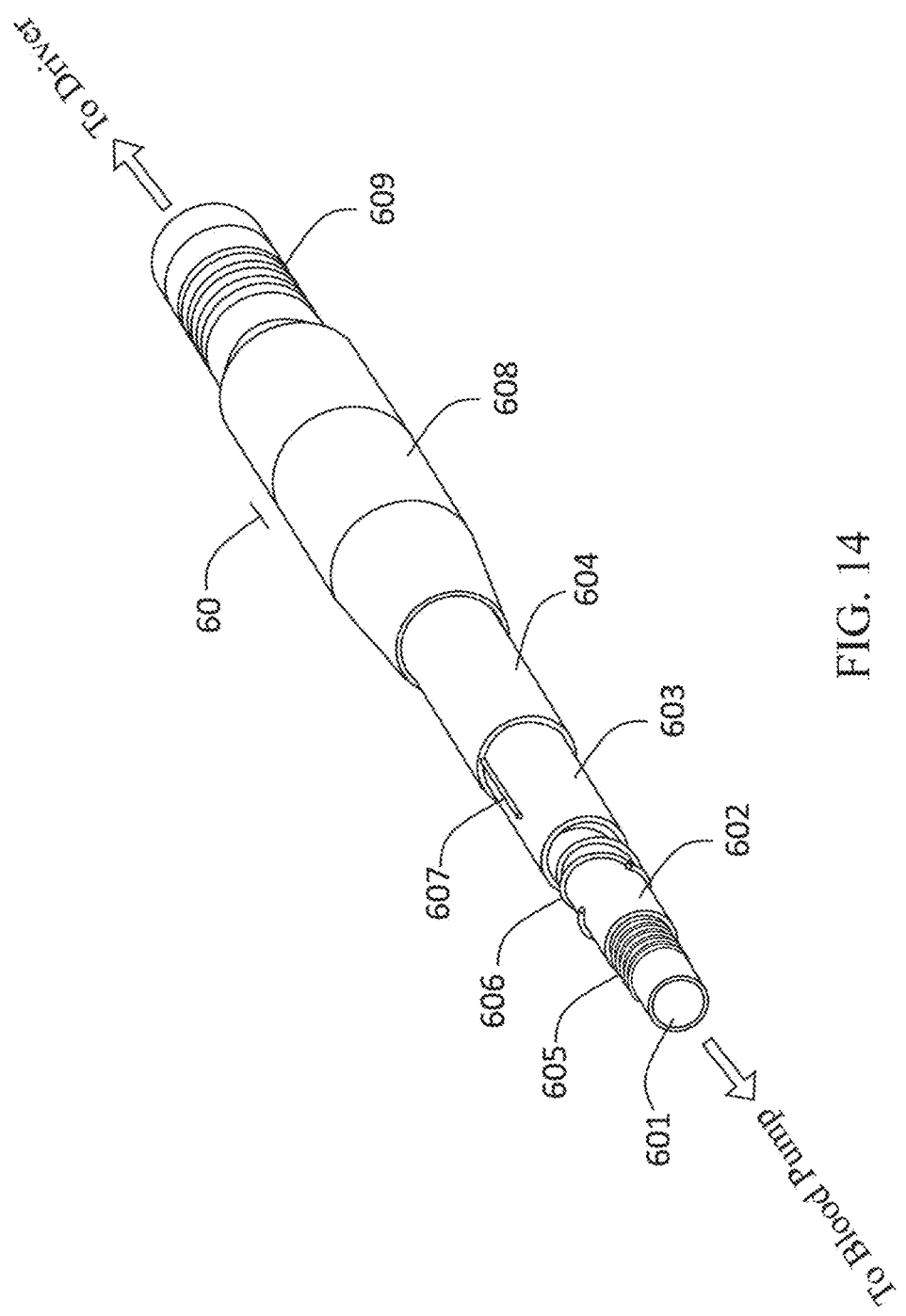
FIG. 14 depicts a representative multi-layered distal driveline (percutaneous lead) that is able to transfer pneumatic pressure pulse and electrical signal between the blood pump and the external driver system.

FIG. 14 shows the structure and components of an exemplary distal driveline 60. The inner lumen 601 is for pneumatic power transport, the first middle layer 602 has a coil reinforcement 605 to prevent driveline kinking, and a tether 607 is disposed in between the second middle lumen 603 and outer silicone jacket 604 for stretch limitation. The electrical wires 606 are spirally wrapped between the first 602 and second 603 middle lumens. At the proximal end is a hollow adapter 608, having electrodes 609 and internal fluid fitting to facilitate driving air transport and electrical signal transduction. There exist numerous designs for pneumatically and electrically communicating blood pump 50 with driver 70. Illustrated in FIG. 1 is an exemplified embodiment which includes the driveline assembly 60A having a distal driveline 60, a proximal driveline 61 and a driveline interconnector 62. The rationale and detail design of this blood pump and driveline modules is disclosed in U.S. application No. 63/162,086 and U.S. application No. 63/125,093.

Figure 15:
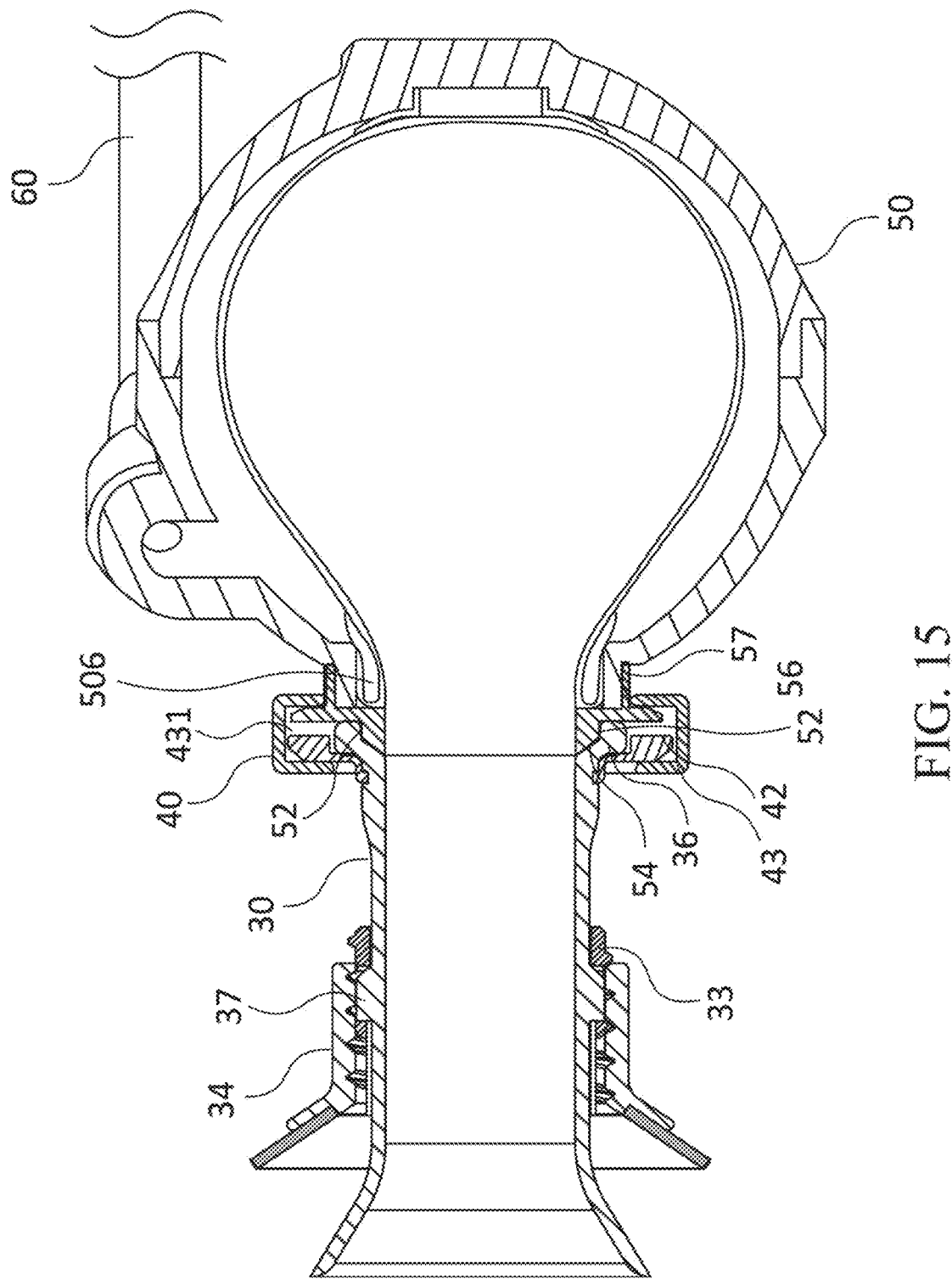
FIG. 15 is a sectional view of the assembled EVBP modules showing coupler in a locked position connecting flow cannula, coupler flange base, and EVBP inlet adapter. Note that the outside surface covering of the flow cannula is not shown for clarity.

FIG. 15 illustrates the integration of the present EVBP 50 in connection with the flow cannula 30 by the coupler 40. The internal grooved slot 431 of the collars 43 receives and compresses together the flange base 42, the flange ramp 36 of the flow cannula 30, and the beak flange 56 of the inlet adapter 30. The collars 43 clamp together flange base 42 and the beak flange 56 while the sandwiched flange ramp 36 is compressed with a predetermined strain. It is observed that the flange ramp 36 of the flow cannula 30 serves as a "gasket" compressed with a controlled strain to attain the sealing effect. Co-pulsatile cardiac support augments LV systolic pressure by design, therefore, having a reliable seal at joint interface is of paramount importance. The fastener pair 33, 34 exerting compression locking mechanism against the clamped epicardium, and the coupler 40 imposing sealed coupling with the semi-rigid cannula are the two novel interface designs to accomplish the purpose of a reliable, leakage-free connection.

Figure 16A:
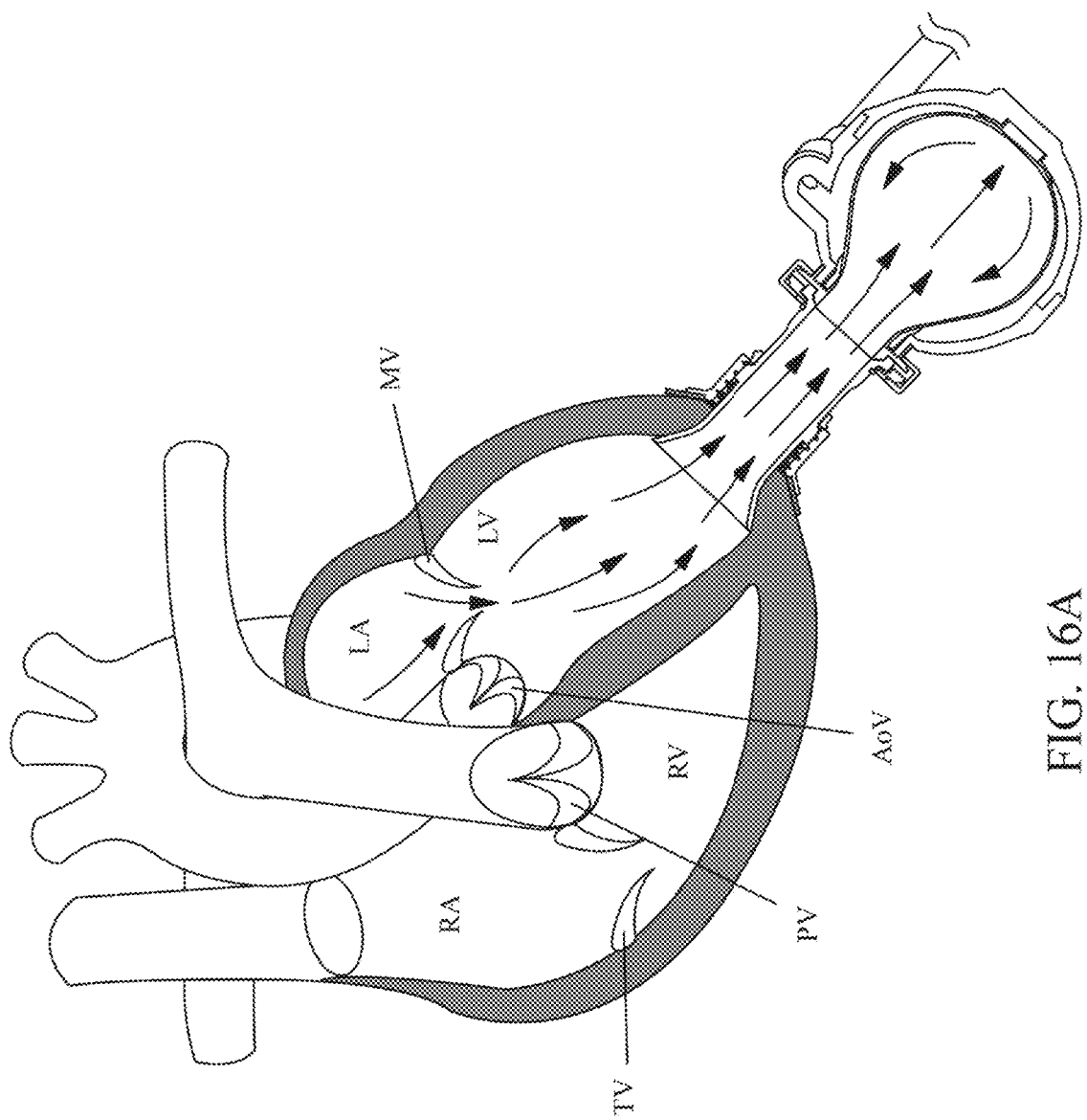
FIG. 16A illustrates the LV chamber extension effect provided by the co-pulsatile EVBP invention during heart diastole (wherein, LA: left atrium, LV: left ventricle, RA: right atrium, RV: right ventricle, AoV: aortic valve, MV: mitral valve, TV: tricuspid valve, and PV: pulmonary valve).
Figure 16B:
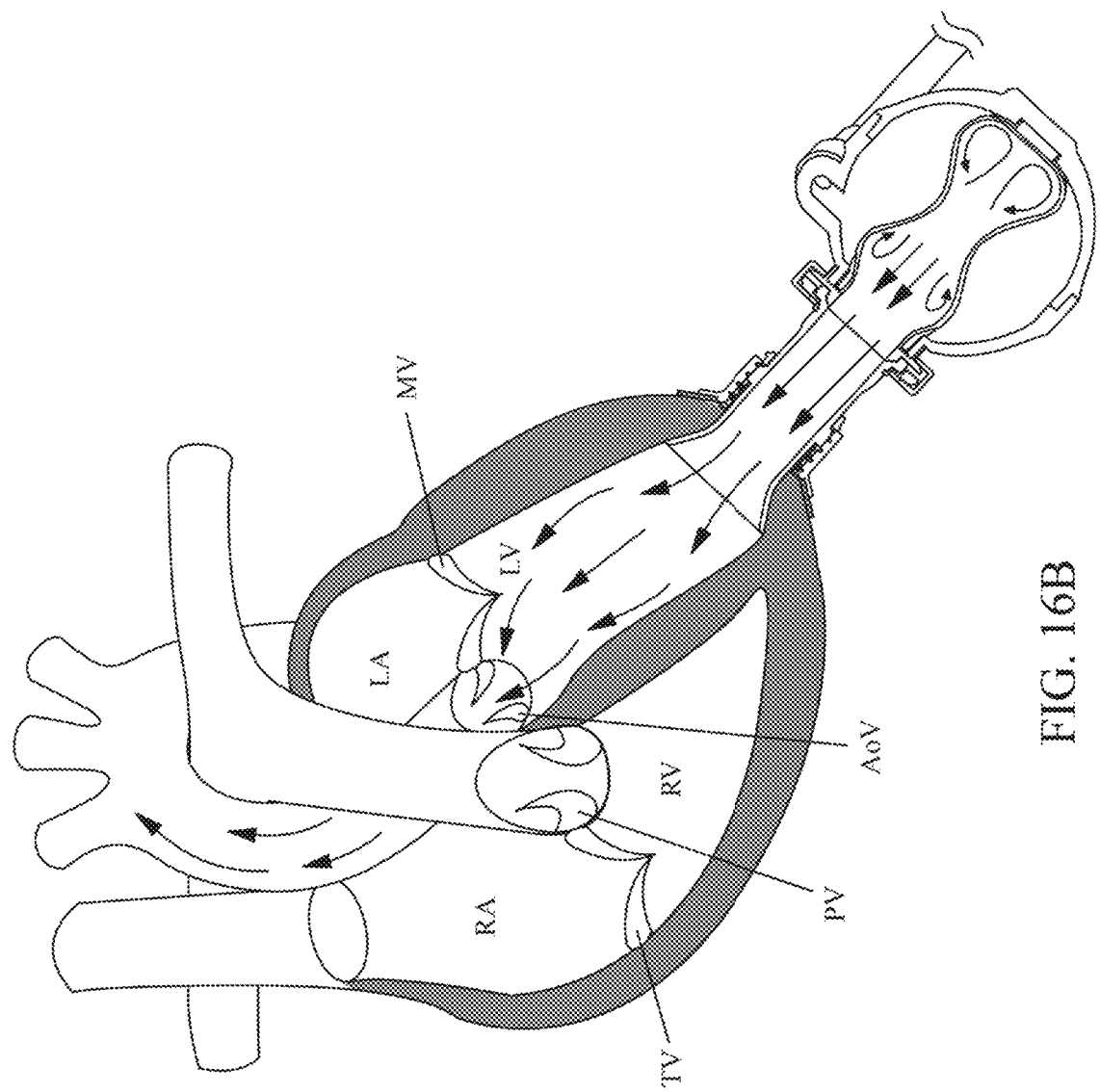
FIG. 16B illustrates the LV ejection augmentation and stroke volume enhancement effect provided by the co-pulsatile EVBP invention during heart systole (wherein, LA: left atrium, LV: left ventricle, RA: right atrium, RV: right ventricle, AoV: aortic valve, MV: mitral valve, TV: tricuspid valve, and PV: pulmonary valve).

Structurally, as seen from FIG. 16A, the blood sac of the connected EVBP 50 becomes an extension of the LV cavity, compensating for the chamber volume loss due to thickened and stiffened LV wall associated with HFpEF. With the aid of a coordinated blood sac filling and ejection action, the EVBP 50 is able to act as a reservoir to accommodate blood flowing in from the left atrium during diastole, thereby compensate for the LV filling dysfunction. This reservoir of blood is then pumped back into the LV during systole, as shown in FIG. 16B, thereby increases the LV stroke volume and the cardiac out.

Figure 17A:
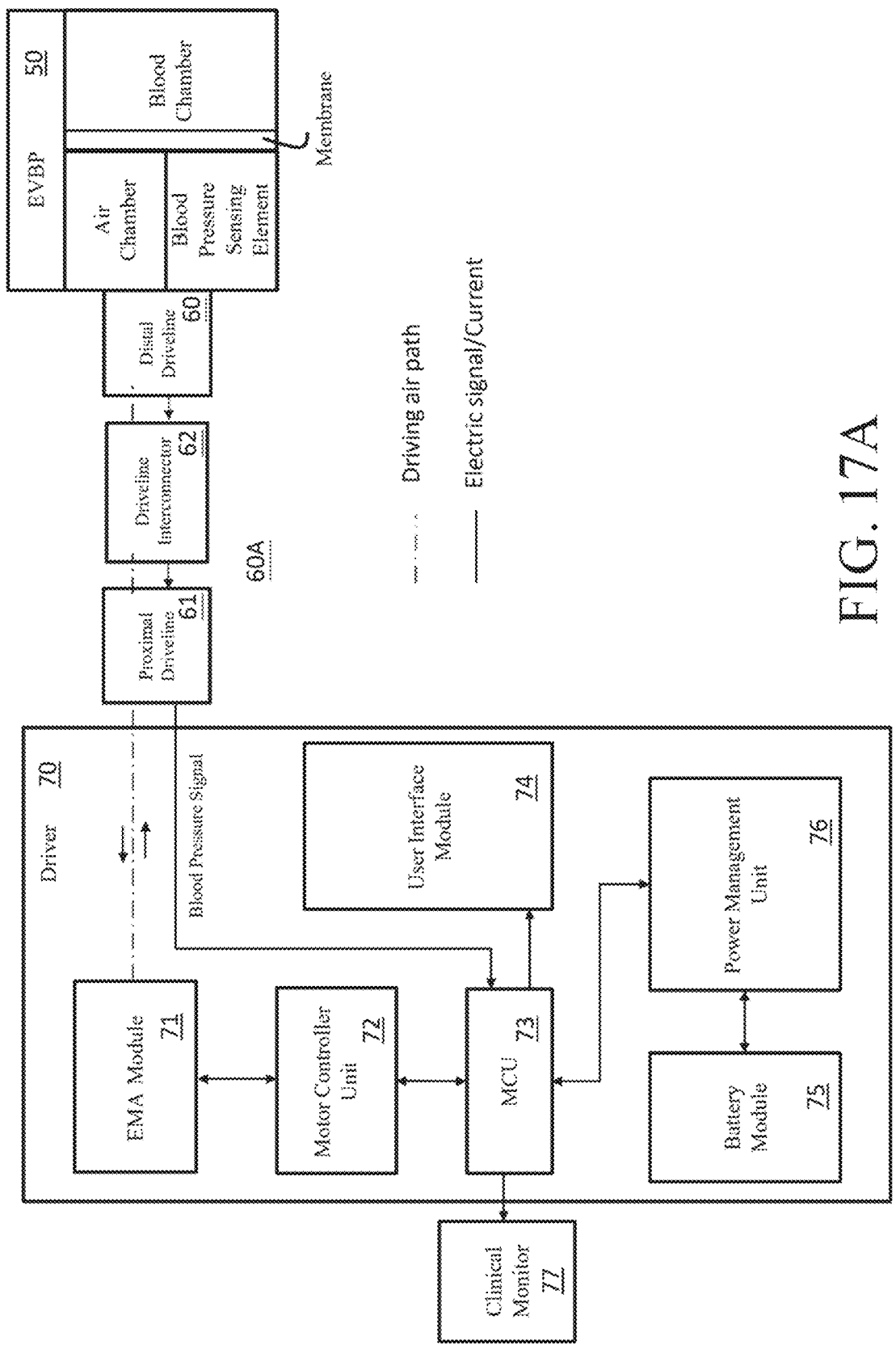
FIG. 17A is a schematic of an electromechanical actuator and a motor controller controlling EVBP pumping in reference to the signal obtained from a pressure sensor embedded in the EVBP housing.
Figure 17B:
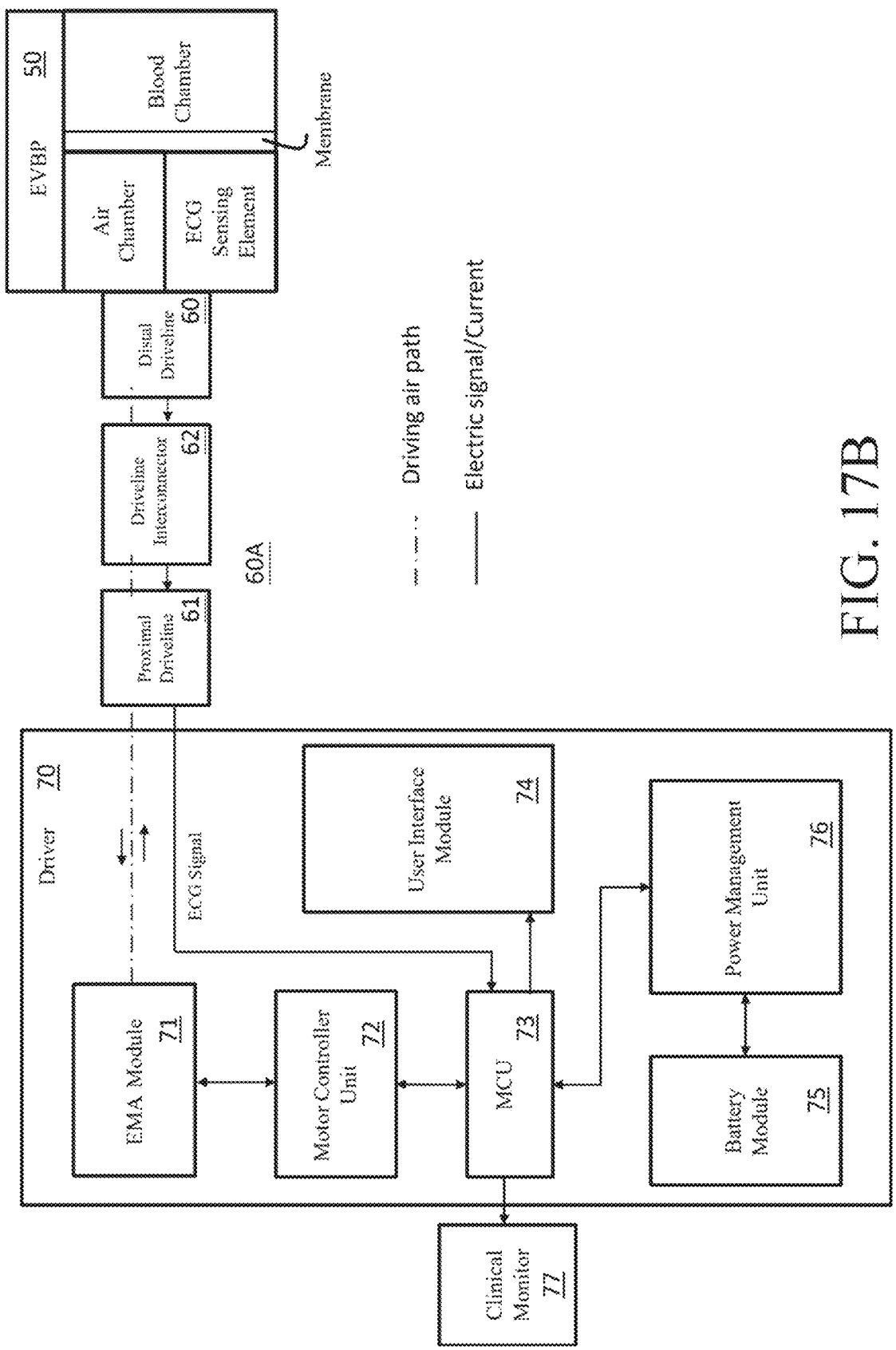
FIG. 17B is a schematic of an electromechanical actuator and a motor controller controlling EVBP pumping in reference to the signal obtained from an electrocardiogram sensor system equipped with the EVBP.

A representative embodiment of the co-pulsatile driver system design is schematically disclosed in FIGS. 17A and 17B. The pneumatic energy converter is disposed in the driver 70, comprising an electromechanical actuator (EMA) 71, a motor controller unit 72, a micro controller unit (MCU) 73, a power management unit 76, a battery module 75 including a main battery and a reserve battery. The signal acquisition, transmission, processing, and the control logic and command generation and EMA actuation to produce pressure pulse to drive the blood pump is illustrated in FIGS. 17A and 17B for the exemplified embodiments.

FIG. 17A shows a pressure-based co-pulsatile pumping scheme. The blood pump pressure sensor assembly 507 is built into the proximal blood pump shell 502 (FIG. 13), allowing a continuous monitoring of the blood pump pressure. A distal driveline (percutaneous lead) 60 is attached to the pump housing 501 and provides timed air pressure pulses to command ejection and filling of the blood sac. The distal and proximal drivelines 60, 61 provide a pneumatically driven pressure, generated by the EMA 71 inside the driver 70, to the blood pump 50; and transmits an electric blood pressure signal, generated by the blood pump pressure sensor 507, to the driver 70. A driving air path (indicated by a dotted arrow line) and an electric signal path (indicated by a double arrow solid-line) is illustrated to describe the functional relationship among the interacted modules. The controller circuit can include a motor controller unit 72 for driving the brushless motor and a micro controller unit (MCU) 73 as a central processor to process the received pressure signal and generate control commands for motor controller to actuate piston motion.

In some embodiments, the co-pulsatile driver 70, commanding a pneumatic pumping support according to a sensed heart rhythm waveform, wherein a co-pulsatile pumping is fulfilled by a pump ejection during systolic ventricular contraction and pump fill during diastolic ventricular relaxation. In some embodiments, the co-pulsatile pumping is fulfilled by referencing to the ECG waveform acquired by the embedded ECG leads with electrodes disposed around or on the outer surface of the blood pump housing 501.

The driver is powered by a main battery and a reserve battery, whereas the reserve battery ensures a continuous power supply of the driver when the main battery is exhausted or removed for recharging. Power can also be supplied to the driver by an AC adapter for the convenience of the patient implanted with the device when mobility is not required.

The EMA 71 is a pneumatic actuator consisting of a brushless servo motor and a ball screw piston/cylinder assembly. Atmospheric air is used as a driving medium to reciprocally eject and fill the blood pump 50.

The driver receives blood pump pressure or ECG signal (electric signal) and processes the signal using trigger detection algorithm to generate trigger signal that commands the driver actuation in synchronization with the heart rhythm. Upon receiving the assigned trigger timing, the MCU sends commands to the motor controller 72 to drive the piston, from eject-to-fill or from fill-to-eject positions, to provide co-pulsatile circulatory support. The motor controller unit 72, however, is a motor servo control system that responds to serial commands sent from MCU to drive the motor with specified position, velocity and acceleration parameters.

The EMA 71 is housed within the driver 70 carried by the implant recipient. The EMA 71 consists of a motor and a ball screw/nut unit that drive a reciprocating piston motion in a cylinder. The stroke motion of the piston drives air to and from the implanted blood pump 50 via a pneumatic driveline 60. The EMA 71 incorporates a pressure equalization valve connected to the cylinder chamber for air replenishment and moisture reduction. The said valve is opened periodically, allowing air mass transport between the cylinder and the ambient until air pressure in the cylinder chamber equals the atmospheric pressure. The EMA incorporates position and optical sensors to acquire reference signals for the electronic controller to generate control command to drive the piston motion.

Figure 18:
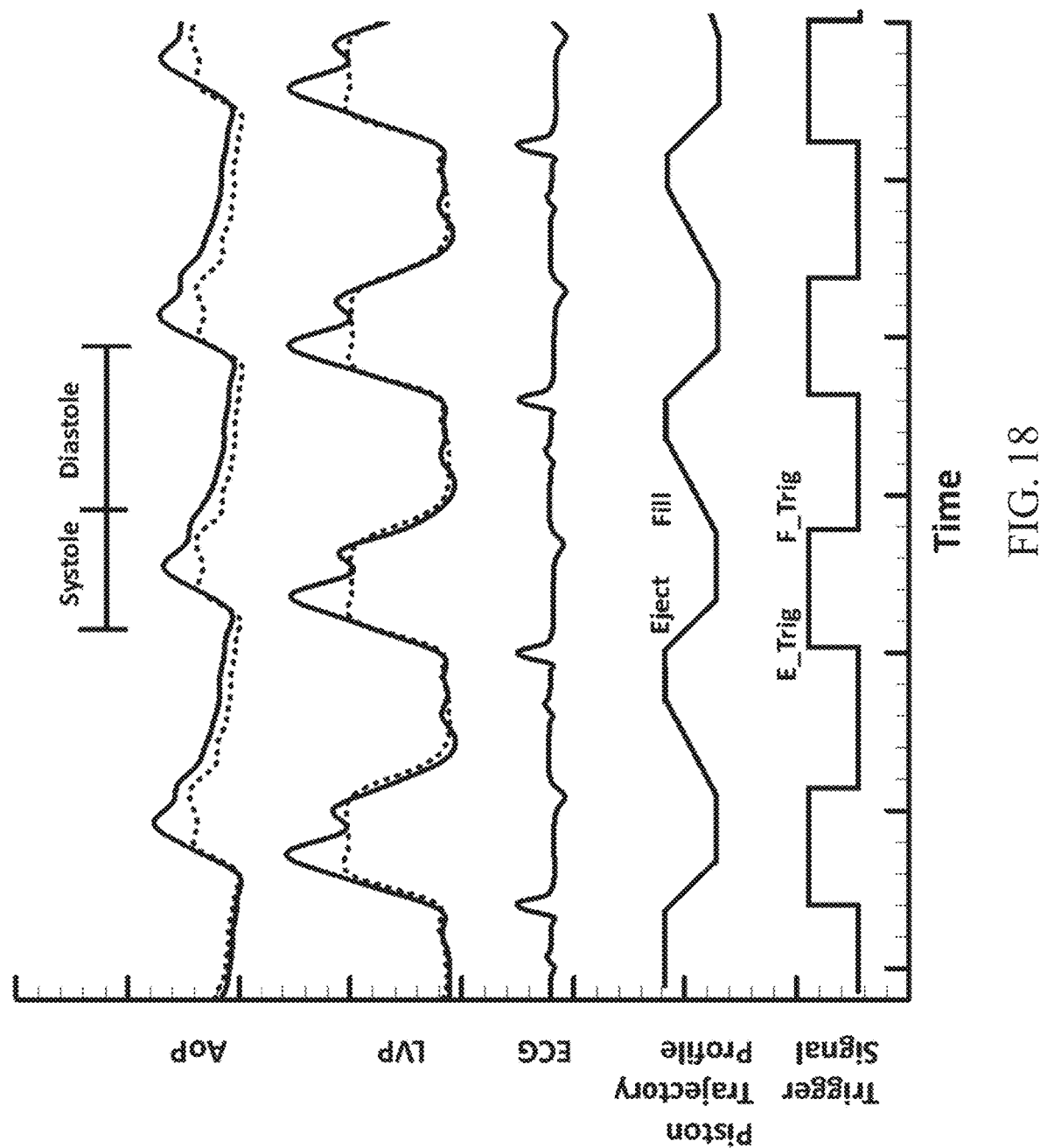
FIG. 18 shows the co-pulsatile relationships among left ventricular pressure (LVP), aortic pressure (AoP), electrocardiogram (ECG) and the piston displacement trajectory of the electromechanical actuator in driving the EVBP circulatory support system. Solid and dotted lines represent assisted and unassisted conditions, respectively.

FIG. 18 depicts the trigger commands for EMA piston position in relation to the co-pulsatile pumping. The design of the trigger detection algorithm is guided by the co-pulsatile requirement, namely, upon detection of ventricular end-diastolic timing, pump ejects when LV starts ejection, followed by pump fill when aortic valve closes and LV starts to undergo isovolumic relaxation until the end-diastolic time point is detected. In FIG. 18 the unassisted aortic pressure (AoP) waveform is expressed in dotted line whereas solid line represents the assisted aortic pressure waveform. The MCU 73 monitors blood pump pressure (BPP) or ECG signal (electric signal) and detects the left ventricle end-diastole (LVED) timing or the R-wave. Upon detection of LVED timing, the MCU generates a E_Trig signal. The time interval between two consecutive E_Trig signals represents an instantaneous cardiac cycle interval (or period). Based on an estimated heart rate calculated from the cycle intervals, the MCU determines the timing, the F_Trig signal, for blood pump filling. When the ejection stroke is completed and after an optimized dwell time elapse (or pause), the EMA is commanded to perform a fill action with a prespecified filling speed upon receiving the F_Trig signal.

In summary, an embodiment of the present invention provides a flow cannula assembly, configured to connect a ventricular chamber of a heart and a blood bump assembly, including a flow cannula and a pair of male fastener and female fastener. The flow cannula includes a conduit body, a bellmouth and a flange ramp portion, wherein the conduit body is between the bellmouth and the flange ramp portion. The bellmouth is at a first end of the flow cannula and is configured to be inserted into the ventricular chamber, and the flange ramp portion is at a second end of the flow cannula and is configured to be interfaced to the blood bump assembly, and an inner surface of the flow cannula is smooth and seamless. The pair of male fastener and female fastener is screw interconnected, wherein the male fastener is anchored on the flow cannula, and the female fastener is compressed against an epicardium of the heart. Imposing sealed coupling with both ends of the semi-rigid cannula constitutes the two novel interface designs to accomplish the purpose of a reliable, leakage-free connection.

Another embodiment of the present invention provides an implantable circulatory support system, including a valveless displacement blood pump, a deformable polymeric flow cannula, a pair of male and female fasteners, a coupler, a driveline assembly, and a co-pulsatile driver. The blood pump includes a blood sac, a blood pump housing, a stem suspension integrating the blood sac within the blood pump housing, a sensor embedded in the blood pump housing to represent a heart rhythm, and an inlet adapter with a beak flange. The flow cannula includes a conduit body, a bellmouth and a flange ramp, wherein the conduit body is between the bellmouth and the flange ramp. The bellmouth is at a first end of the flow cannula and is configured to be inserted into a heart chamber, and the flange ramp portion is at a second end of the flow cannula and is configured to be interfaced to the inlet adapter, and an inner surface of the flow cannula is smooth and seamless. The pair of male and female fasteners is screw interconnected, wherein the male fastener is anchored on the flow cannula, and the female fastener is compressed against the epicardium of the heart. The coupler connects the second end of the flow cannula with the inlet adapter, wherein the coupler includes a flange base and a pair of collars pinned on the flange base, wherein the collars have an internal grooved slot to receive and compress together the flange base, the flange ramp of the flow cannula, and the beak flange of the inlet adapter. The driveline assembly pneumatically communicates the blood pump with as well as transmits a heart rhythm signal to the driver. The co-pulsatile driver commands a pneumatic pumping support according to a sensed heart rhythm waveform, wherein a co-pulsatile pumping is fulfilled by pump ejection during systolic ventricular contraction and pump fill during diastolic ventricular relaxation.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

It will be apparent to those skilled in the art that various modifications and variations can be made in the invention. It is intended that the standard and examples be considered as exemplary only, with the true scope of the disclosed embodiments being indicated by the following claims and their equivalents.

What is claimed is:

1. An implantable circulatory support system, configured to connect a ventricular chamber of a heart, comprising:
   a blood pump, including a blood sac, a blood pump housing, a stem suspension integrating the blood sac within the blood pump housing, a sensor embedded in the blood pump housing to represent a heart rhythm, and an inlet adapter with a beak flange;
   a flow cannula assembly, comprising:
      a deformable flow cannula, including a conduit body, a bellmouth and a flange ramp, wherein the conduit body is between the bellmouth and the flange ramp, the bellmouth is at a first end of the flow cannula and is configured to be inserted into the ventricular chamber, the flange ramp is at a second end of the flow cannula and is configured to be interfaced to the blood pump, and an inner surface of the flow cannula is smooth and seamless;
      a male fastener and a female fastener, being screw interconnected, wherein the male fastener is anchored on the flow cannula, and the female fastener is compressed against an epicardium of the ventricular chamber; and
      a coupler, connecting the second end of the flow cannula with the inlet adapter of the blood pump, and comprises a flange base and a pair of collars pinned on the flange base, wherein the collars have an internal grooved slot to receive and compress together the flange base, the flange ramp of the flow cannula, and the beak flange of the inlet adapter;
   a driveline assembly; and
   a co-pulsatile driver,
   wherein the driveline assembly pneumatically communicates the blood pump with as well as transmits a heart rhythm signal to the driver;
   wherein the co-pulsatile driver commands a pneumatic pumping support according to a sensed heart rhythm waveform, wherein a co-pulsatile pumping is fulfilled by a pump ejection during systolic ventricular contraction and a pump fill during diastolic ventricular relaxation.

2. The implantable circulatory support system as claimed in claim 1, wherein the beak flange of the inlet adapter has a beak interfacing with the flange ramp, an inner diameter of the beak slightly larger than an inner diameter of the conduit body, and the flange ramp is inclined 30 to 60 degrees to a centerline of the flow cannula.

3. The implantable circulatory support system as claimed in claim 1, wherein the coupler includes an anti-decoupling latch and a collar contour that catches simultaneously onto an entire peripheral rim of the flange base of the coupler.

4. The implantable circulatory support system claimed in claim 1, wherein the co-pulsatile pumping is fulfilled by referencing to an electrocardiogram waveform measured from the heart.

5. The implantable circulatory support system as claimed in claim 1, wherein the sensor is a pressure sensor, such that the co-pulsatile pumping is fulfilled by referencing to a pressure waveform acquired by the sensor.

6. The implantable circulatory support system as claimed in claim 1, wherein the stem suspension has a pair of axi-symmetric stems, and the blood sac of the blood pump is made to be axi-symmetric, thereby being supported by the pair of axi-symmetric stems.

* * * * *